(12) United States Patent
Yokoyama et al.

(10) Patent No.: US 9,306,175 B2
(45) Date of Patent: Apr. 5, 2016

(54) ORGANIC ELECTROLUMINESCENT DEVICE

(75) Inventors: Norimasa Yokoyama, Tokyo (JP);
Makoto Nagaoka, Tsukuba (JP);
Kazunori Togashi, Tokyo (JP); Shigeru Kusano, Tsukuba (JP); Eiji Takahashi, Tsukuba (JP)

(73) Assignee: Hodogaya Chemical Co., Ltd., Tokyo (JP)

( * ) Notice: Subject to any disclaimer, the term of this patent is extended or adjusted under 35 U.S.C. 154(b) by 1018 days.

(21) Appl. No.: 13/503,186
(22) PCT Filed: Oct. 22, 2010
(86) PCT No.: PCT/JP2010/006285
§ 371 (c)(1),
(2), (4) Date: Apr. 20, 2012
(87) PCT Pub. No.: WO2011/048822
PCT Pub. Date: Apr. 28, 2011

(65) Prior Publication Data
US 2012/0205642 A1     Aug. 16, 2012

(30) Foreign Application Priority Data

Oct. 23, 2009    (JP) ................................ 2009-244247

(51) Int. Cl.
*H01L 51/50*     (2006.01)
*H01L 51/00*     (2006.01)
(Continued)

(52) U.S. Cl.
CPC .......... *H01L 51/0072* (2013.01); *C07D 209/86* (2013.01); *C07D 209/88* (2013.01);
(Continued)

(58) Field of Classification Search
None
See application file for complete search history.

(56) References Cited

U.S. PATENT DOCUMENTS

2003/0137239 A1*   7/2003   Matsuura et al. ............. 313/503
2004/0170863 A1*   9/2004   Kim et al. ..................... 428/690
(Continued)

FOREIGN PATENT DOCUMENTS

CN       1762182 A     4/2006
CN     101515632 A     8/2009
(Continued)

OTHER PUBLICATIONS

Park et al., Synthesis and electroluminescent properties of para- and meta-tolyl carbazyl derivatives, 2006, Thin Solid Films, vol. 209, pp. 127-131.*

(Continued)

*Primary Examiner* — Gregory Clark
(74) *Attorney, Agent, or Firm* — Locke Lord LLP; James E. Armstrong, IV; Nicholas J. DiCeglie, Jr.

(57) ABSTRACT

A high-efficiency, high-durability organic electroluminescent device, particularly a phosphorescent organic electroluminescent device is provided by using an organic compound of excellent characteristics that exhibits excellent hole-injecting/transporting performance and has high triplet exciton confining capability with an electron blocking ability, and that has high stability in the thin-film state and high luminous efficiency.

The organic electroluminescent device includes a pair of electrodes, and a plurality of organic layers sandwiched between the pair of electrodes and including a phosphorescent light-emitting material-containing light emitting layer and a hole transport layer, wherein a compound of the following general formula (1) having a carbazole ring structure is used as a constituent material of the hole transport layer.

[Chemical Formula 1]

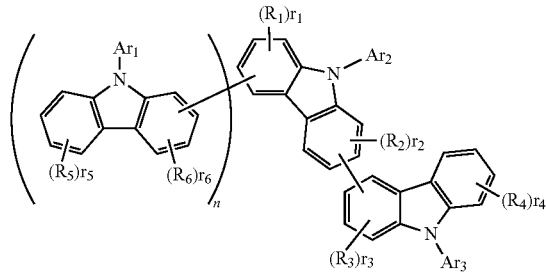

13 Claims, 2 Drawing Sheets

← 9 CATHODE
← 8 ELECTRON INJECTION LAYER
← 7 ELECTRON TRANSPORT LAYER
← 6 HOLE BLOCKING LAYER
← 5 LIGHT EMITTING LAYER
← 4 HOLE TRANSPORT LAYER
← 3 HOLE INJECTION LAYER
← 2 TRANSPARENT ANODE
← 1 GLASS SUBSTRATE

(51) Int. Cl.
    *C07D 209/86* (2006.01)
    *C07D 209/88* (2006.01)
    *C07D 403/04* (2006.01)
    *C07D 409/04* (2006.01)
    *C07D 471/04* (2006.01)

(52) U.S. Cl.
    CPC ............ *C07D403/04* (2013.01); *C07D 409/04* (2013.01); *C07D 471/04* (2013.01); *H01L 51/5016* (2013.01); *H01L 51/5056* (2013.01); *H01L 51/5088* (2013.01)

(56) References Cited

U.S. PATENT DOCUMENTS

| | | | |
|---|---|---|---|
| 2006/0175960 A1* | 8/2006 | Noh et al. | 313/505 |
| 2006/0180806 A1 | 8/2006 | Arakane et al. | |
| 2008/0242871 A1 | 10/2008 | Kawakami et al. | |
| 2008/0305287 A1 | 12/2008 | Ohata et al. | |
| 2009/0115320 A1* | 5/2009 | Kawamura et al. | 313/504 |
| 2009/0206742 A1 | 8/2009 | Oda et al. | |
| 2009/0302745 A1 | 12/2009 | Otsu et al. | |

FOREIGN PATENT DOCUMENTS

| | | |
|---|---|---|
| EP | 1589789 A1 | 10/2005 |
| EP | 2471771 A1 | 7/2012 |
| JP | 08-003547 A | 1/1996 |
| JP | 09-249876 A | 9/1997 |
| JP | 11-144876 A | 5/1999 |
| JP | 2009-218568 A | 9/2009 |
| KR | 2009-0028943 A | 3/2009 |
| WO | WO-2004/066685 A1 | 8/2004 |
| WO | WO-2007/015465 A1 | 2/2007 |
| WO | WO-2007/119816 A1 | 10/2007 |

OTHER PUBLICATIONS

Office Action mailed Feb. 3, 2015, issued for the Japanese patent application No. 2011-537148.

International Search Report dated Dec. 28, 2010, issued for PCT/JP2010/006285.

Office Action dated Jul. 8, 2014, issued for the corresponding Chinese patent application No. 201080047863.4 and Japanese translation thereof.

Supplementary European Search Report Dated Nov. 12, 2013, issued for the corresponding European patent application No. 10824674.5.

Office Action dated Oct. 21, 2014, issued for the corresponding Taiwanese patent application No. 099136330 and Japanese translation thereof.

Office Action mailed Oct. 21, 2014, issued for the corresponding Japanese patent application No. 2011-537148.

* cited by examiner

ORGANIC ELECTROLUMINESCENT DEVICE

CROSS REFERENCE TO RELATED APPLICATIONS

This application is related to co-pending application: "ORGANIC ELECTROLUMINESCENT DEVICE" filed even date herewith in the names of Norimasa Yokoyama; Makoto Nagaoka; Kazunori Togashi; Shigeru Kusano; and Eiji Takahashi as a national phase entry of PCT/JP2010/006284 field Oct. 22, 2010, which application is assigned to the assignee of the present application and is incorporated by reference herein.

TECHNICAL FIELD

The present invention relates to organic electroluminescent devices (hereinafter, simply referred to as "organic EL devices"), preferred self light-emitting devices for various display devices. Specifically, the invention relates to organic EL devices that use compounds having a carbazole ring structure.

BACKGROUND ART

The organic EL device is a self-emitting device, and has been actively studied for their brighter, superior viewability and ability to display clearer images compared with the liquid crystal device.

In 1987, C. W. Tang et al. at Eastman Kodak developed a laminated structure device using materials assigned with different roles, realizing practical applications of an organic EL device with organic materials. These researchers laminated tris(8-hydroxyquinoline)aluminum (an electron-transporting phosphor; hereinafter, simply $Alq_3$), and a hole-transporting aromatic amine compound, and injected the both charges into the phosphor layer to cause emission in order to obtain a high luminance of $1,000$ cd/m$^2$ or more at a voltage of 10 V or less (see, for example, Patent Documents 1 and 2).

To date, various improvements have been made for practical applications of the organic EL device. In order to realize high efficiency and durability, various roles are further subdivided to provide an electroluminescent device that includes an anode, a hole injection layer, a hole transport layer, a light emitting layer, an electron transport layer, an electron injection layer, and a cathode successively formed on a substrate (see, for example, Non-Patent Document 1).

Further, there have been attempts to use triplet excitons for further improvements of luminous efficiency, and use of phosphorescent materials have been investigated (see, for example, Non-Patent Document 2).

The light emitting layer can also be fabricated by doping a charge-transporting compound, generally called a host material, with a phosphor or a phosphorescent material. As described in the foregoing lecture preprints, selection of organic materials in an organic EL device greatly influences various device characteristics, including efficiency and durability.

In an organic EL device, the charges injected from the both electrodes recombine at the light emitting layer to cause emission. The probability of hole-electron recombination can be improved by improving the hole injectability and the electron blocking performance of blocking the injected electrons from the cathode, and high luminous efficiency can be obtained by confining the excitons generated in the light emitting layer. The role of the hole transport material is therefore important, and there is a need for a hole transport material that has high hole injectability, high hole mobility, high electron blocking performance, and high durability to electrons.

The aromatic amine derivatives described in Patent Documents 1 and 2 are known examples of the hole transport materials used for the organic EL device. These compounds include a compound known to have an excellent hole mobility of $10^{-3}$ cm$^2$/Vs or higher. However, the compound is insufficient in terms of electron blocking performance, and some of the electrons pass through the light emitting layer. Accordingly, improvements in luminous efficiency cannot be expected.

Arylamine compounds of the following formulae having a substituted carbazole structure (for example, Compounds A, B, and C) are proposed as improvements over the foregoing compounds (see, for example, Patent Documents 3 to 5).

[Chemical Formula 1]

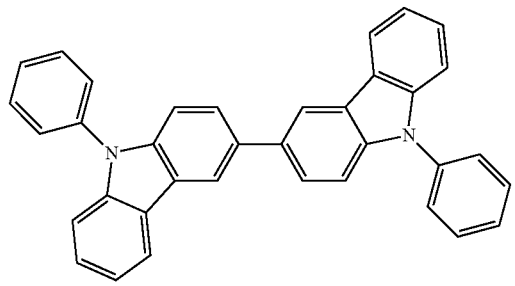

(Compound A)

[Chemical Formula 2]

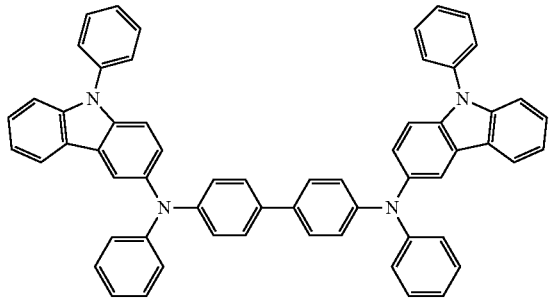

(Compound B)

[Chemical Formula 3]

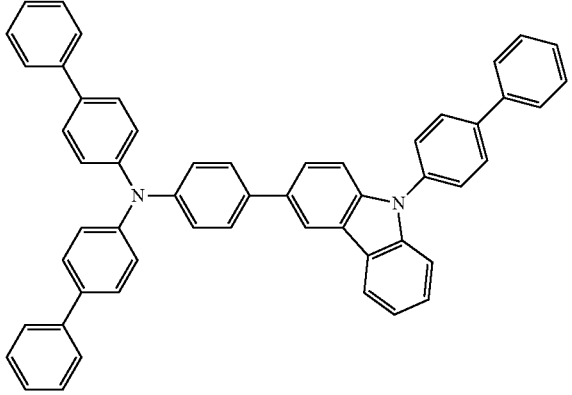

(Compound C)

In an attempt to improve the device luminous efficiency, there have been developed devices that use phosphorescent materials to generate phosphorescence, specifically that make use of the emission from the triplet excitation state. According to the excitation state theory, phosphorescent materials are expected to greatly increase luminous efficiency about four times as much as that of the conventional fluorescence.

In 1999, M. A. Baldo et al. at Princeton University realized 8% luminous efficiency with a phosphorescent device using an iridium complex, a great improvement over the conventional external quantum efficiency. The phosphorescent device has been actively developed ever since.

Improving the luminous efficiency of the phosphorescent device requires use of materials of high excitation triplet energy level (hereinafter, simply "$T_1$") for the host material. However, there is a report that use of materials with high $T_1$ is also necessary for the hole transport material to confine the triplet excitons (see, for example, Non-Patent Document 3). Further, the green phosphorescent material tris(phenylpyridyl)iridium (hereinafter, simply "Ir(ppy)$_3$") represented by the following formula has a $T_1$ of 2.42 eV.

[Chemical Formula 4]

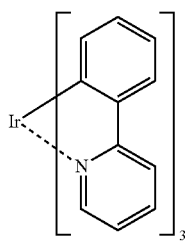

Because N,N'-diphenyl-N,N'-di(α-naphthyl)benzidine (hereinafter, simply "α-NPD") has a $T_1$ of 2.29 eV, sufficient confinement of the triplet excitons cannot be expected with α-NPD. Higher luminous efficiency is thus obtained using 1,1-bis[4-(di-4-tolylamino)phenyl]cyclohexane (hereinafter, simply "TAPC") of the following formula having a higher $T_1$ value of 2.9 eV (see, for example, Non-Patent Document 4).

[Chemical Formula 5]

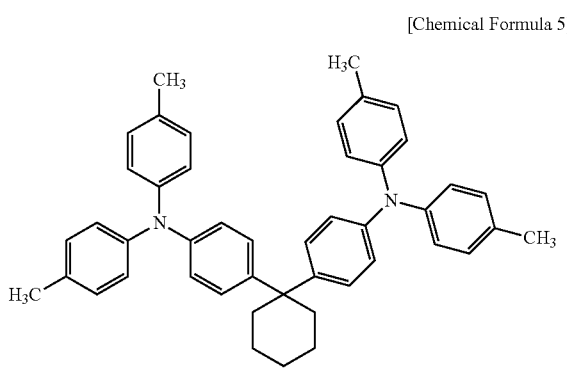

However, the TAPC has low hole mobility, and its ionization potential (work function) 5.8 eV is not appropriate for a hole transport material.

The ionization potential (work function) of Compound A is 5.5 eV, a more appropriate value compared to the ionization potential of the TAPC. It is expected that this, combined with the high $T_1$ of 2.9 eV, would provide sufficient confinement of the triplet excitons. However, because the compound has low hole mobility, the product device has high driving voltage, and the luminous efficiency cannot be said as sufficient (see, for example, Non-Patent Document 5). Accordingly, there is a need for materials having a high $T_1$ value and high hole mobility that can be used as a hole injection layer or a hole transport layer, in order to obtain a phosphorescent device having improved luminous efficiency.

CITATION LIST

Patent Documents

Patent Document 1: JP-A-8-048656
Patent Document 2: Japanese Patent Number 3194657
Patent Document 3: JP-A-8-003547
Patent Document 4: JP-A-2006-151979
Patent Document 5: WO2008/62636
Patent Document 6: JP-A-2007-022986

Non-Patent Documents

Non-Patent Document 1: The Japan Society of Applied Physics, 9th lecture preprints, pp. 55 to 61 (2001)
Non-Patent Document 2: The Japan Society of Applied Physics, 9th lecture preprints, pp. 23 to 31 (2001)
Non-Patent Document 3: J. Appl. Phys., 12, 95, 7798 (2004)
Non-Patent Document 4: Organic EL Display, 89 (2004), Tokitoh, Adachi, Murata, Ohmsha
Non-Patent Document 5: Appl. Phys. Lett., 93, 063306 (2008)
Non-Patent Document 6: Helvetica Chimica Acta., vol. 89, 1123 (2006)
Non-Patent Document 7: J. Org. Chem., 60, 7508 (1995)
Non-Patent Document 8: Synth. Commun., 11, 513 (1981)
Non-Patent Document 9: Jikken Kagaku Kouza 7, 4th ed., pp. 384-398 (1992), The Chemical Society of Japan, Maruzen
Non-Patent Document 10: Organic EL Symposium, the 1st Regular presentation Preprints, 19 (2005)
Non-Patent Document 11: Appl. Phys. Lett., 93, 133312 (2008)

SUMMARY OF THE INVENTION

Problems that the Invention is to Solve

It is an object of the present invention to provide a high-efficient, high-durable organic EL device, particularly a phosphorescent organic EL device, using an organic compound of excellent characteristics that exhibits excellent hole-injecting/transporting performance and has high triplet exciton confining capability with an electron blocking ability, and that has high stability in the thin-film state and high luminous efficiency.

Some of the physical properties of the organic compound used for the organic EL device of the present invention include (1) good hole injection characteristics, (2) high hole mobility, (3) high $T_1$ value, (4) excellent electron blocking ability, (5) stability in the thin-film state, and (6) excellent heat resistance. Some of the physical properties of the organic EL device to be provided by the present invention include (1) high luminous efficiency and high power efficiency, (2) low turn on voltage, and (3) low actual driving voltage.

Means for Solving the Problems

In order to achieve the foregoing objects, the present inventors focused on the high $T_1$ value, the excellent electron blocking performance and excellent hole transporting ability, and the excellent heat resistance and excellent thin film stability of a carbazole ring structure, and produced various test organic EL devices by designing, selecting, and chemically synthesizing compounds linked to a carbazole ring structure. The present invention was completed after thorough evaluations of the device characteristics.

Specifically, the present invention provides the following organic EL devices.

1) An organic EL device that includes a pair of electrodes, and a plurality of organic layers sandwiched between the pair of electrodes and including a phosphorescent light-emitting material-containing light emitting layer and a hole transport layer, wherein a compound of the following general formula (1) having a carbazole ring structure is used as a constituent material of the hole transport layer.

[Chemical Formula 6]

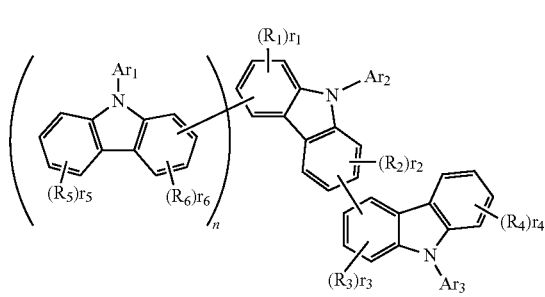

(1)

In the formula, R1, R2, R3, R4, R5, and R6 may be the same or different, and represent a fluorine atom, a chlorine atom, cyano, trifluoromethyl, nitro, linear or branched alkyl of 1 to 6 carbon atoms, cycloalkyl of 5 to carbon atoms, linear or branched alkyloxy of 1 to 6 carbon atoms, cycloalkyloxy of 5 to 10 carbon atoms, a substituted or unsubstituted aromatic hydrocarbon group, a substituted or unsubstituted aromatic heterocyclic group, a substituted or unsubstituted condensed polycyclic aromatic group, or substituted or unsubstituted aryloxy. r1, r4, and r5 represent 0 or an integer of 1 to 4. r2, r3, and r6 represent 0 or an integer of 1 to 3. n represents 0 or an integer of 1. Ar1, Ar2, and Ar3 may be the same or different, and represent a substituted or unsubstituted aromatic hydrocarbon group, a substituted or unsubstituted aromatic heterocyclic group, or a substituted or unsubstituted condensed polycyclic aromatic group.

2) An organic EL device of 1) in which the compound having a carbazole ring structure is used as a constituent material of the hole transport layer, wherein Ar2 in the general formula (1) is a monovalent group represented by the following general formula (2) or (3).

[Chemical Formula 7]

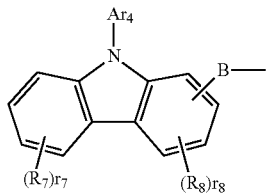

(2)

In the formula, R7 and R8 may be the same or different, and represent a fluorine atom, a chlorine atom, cyano, trifluoromethyl, nitro, linear or branched alkyloxy of 1 to 6 carbon atoms, cycloalkyloxy of 5 to 10 carbon atoms, a substituted or unsubstituted aromatic hydrocarbon group, a substituted or unsubstituted aromatic heterocyclic group, a substituted or unsubstituted condensed polycyclic aromatic group, or substituted or unsubstituted aryloxy. r7 represents 0 or an integer of 1 to 4, and r8 represents 0 or an integer of 1 to 3. B represents a divalent group of a substituted or unsubstituted aromatic hydrocarbon, a divalent group of a substituted or unsubstituted aromatic heterocyclic ring, or a divalent group of a substituted or unsubstituted condensed polycyclic aromatic. Ar4 represents a substituted or unsubstituted aromatic hydrocarbon group, a substituted or unsubstituted aromatic heterocyclic group, or a substituted or unsubstituted condensed polycyclic aromatic group.

[Chemcial Formula 8]

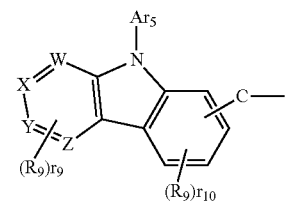

(3)

In the formula, R9 and R10 may be the same or different, and represent a fluorine atom, a chlorine atom, cyano, trifluoromethyl, nitro, linear or branched alkyl of 1 to 6 carbon atoms, cycloalkyl of 5 to 10 carbon atoms, linear or branched alkyloxy of 1 to 6 carbon atoms, cycloalkyloxy of 5 to 10 carbon atoms, a substituted or unsubstituted aromatic hydrocarbon group, a substituted or unsubstituted aromatic heterocyclic group, a substituted or unsubstituted condensed polycyclic aromatic group, or substituted or unsubstituted aryloxy. r9 and r10 represent 0 or an integer of 1 to 3. C represents a divalent group of a substituted or unsubstituted aromatic hydrocarbon, a divalent group of a substituted or unsubstituted aromatic heterocyclic ring, or a divalent group of a substituted or unsubstituted condensed polycyclic aromatic. Ar5 represents a substituted or unsubstituted aromatic hydrocarbon group, a substituted or unsubstituted aromatic heterocyclic group, or a substituted or unsubstituted condensed polycyclic aromatic group. W, X, Y, and Z represent a carbon atom or a nitrogen atom, where only one of W, X, Y, and Z is a nitrogen atom, and, in this case, the nitrogen atom does not have the substituent R9.

3) An organic EL device of 1) or 2), wherein the organic layer is a hole injection layer, and wherein the hole injection layer contains an arylamine compound of a structure in which three or more triphenylamine structures are joined to each other within the molecule via a divalent group that does not contain a heteroatom, or via a single bond.

4) An organic EL device of 3) wherein the arylamine compound of a structure in which three or more triphenylamine structures are joined to each other within the molecule via a divalent group that does not contain a heteroatom, or via a single bond is an arylamine compound represented by the following general formula (4).

[Chemical Formula 9]

(4)

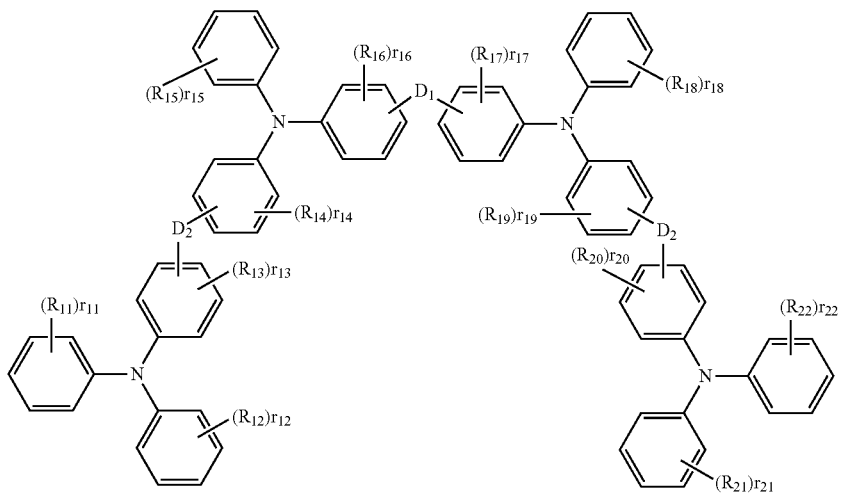

In the formula, R11 to R22 may be the same or different, and represent a fluorine atom, a chlorine atom, cyano, trifluoromethyl, linear or branched alkyl of 1 to 6 carbon atoms, linear or branched alkenyl of 2 to 6 carbon atoms, a substituted or unsubstituted aromatic hydrocarbon group, a substituted or unsubstituted aromatic heterocyclic group, or a substituted or unsubstituted condensed polycyclic aromatic group. These substituents may together form a ring when a plurality of these substituents are joined to the same benzene ring. r11 to r22 represent 0 or an integer of 1 to 4. D1, D2, and D3 may be the same or different, and represent a divalent group of the following structural formulae (E) to (I), or a single bond.

[Chemical Formula 10]

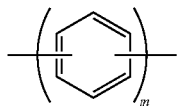

(E)

In the formula, m represents an integer of 1 to 3.

[Chemical Formula 11]

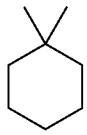

(F)

[Chemical Formula 12]

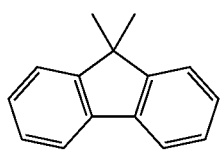

(G)

-continued

[Chemical Formula 13]

(H)

[Chemical Formula 14]

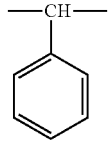

(I)

5) An organic EL device that includes a pair of electrodes, and a plurality of organic layers sandwiched between the pair of electrodes and including a phosphorescent light-emitting material-containing light emitting layer, a hole injection layer, and a hole transport layer, wherein a compound of the general formula (1) having a carbazole ring structure is used as a constituent material of the hole injection layer.

6) An organic EL device of any one of 1) or 5), wherein the phosphorescent light-emitting material is a metal complex that contains iridium or platinum.

Specific examples of the "linear or branched alkyl of 1 to 6 carbon atoms" or the "cycloalkyl of 5 to 10 carbon atoms" represented by R1 to R10 in general formulae (1) to (3) include methyl, ethyl, n-propyl, isopropyl, n-butyl, isobutyl, tert-butyl, n-pentyl, isopentyl, neopentyl, n-hexyl, cyclopentyl, cyclohexyl, 1-adamantyl, and 2-adamantyl.

Specific examples of the "linear or branched alkyloxy of 1 to 6 carbon atoms" or the "cycloalkyloxy of 5 to 10 carbon atoms" represented by R1 to R10 in general formulae (1) to (3) include methyloxy, ethyloxy, n-propyloxy, isopropyloxy, n-butyloxy, tert-butyloxy, n-pentyloxy, n-hexyloxy, cyclopentyloxy, cyclohexyloxy, cycloheptyloxy, cyclooctyloxy, 1-adamantyloxy, and 2-adamantyloxy.

Specific examples of the "aromatic hydrocarbon", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by R1 to R10 or Ar1 to Ar5 in general formulae (1) to (3) include phenyl, biphenylyl, terphenylyl, naphthyl, anthryl, phenanthryl, fluorenyl, indenyl, pyrenyl, acenaphthenyl, fluoranthenyl, triphenylenyl, pyridyl, furanyl, pyranyl, thienyl, quinolyl, isoquinolyl, benzofuranyl, benzothienyl, indolyl, carbazolyl, benzooxazolyl, benzothiazolyl, quinoxalyl, benzoimidazolyl, pyrazolyl, dibenzofuranyl, dibenzothienyl, and carbolinyl, of which phenyl, biphenylyl, terphenylyl, fluorenyl, carbazolyl, and carbolinyl are preferable. Preferably, the "condensed polycyclic aromatic" has 20 or less carbon atoms, because $T_1$ becomes smaller as the number of carbon atoms in the "condensed polycyclic aromatic" increases.

Specific examples of the "substituent" in the "substituted aromatic hydrocarbon", the "substituted aromatic heterocyclic group", or the "substituted condensed polycyclic aromatic" represented by R1 to R10 or Ar1 to Ar5 in general formulae (1) to (3) include a fluorine atom, a chlorine atom, cyano, trifluoromethyl, nitro, linear or branched alkyl of 1 to 6 carbon atoms, cycloalkyl of 5 to 10 carbon atoms, linear or branched alkenyl of 2 to 6 carbon atoms, linear or branched alkyloxy of 1 to 6 carbon atoms, cycloalkyloxy of 5 to 10 carbon atoms, phenyl, naphthyl, anthryl, styryl, phenoxy, tolyloxy, benzyloxy, and phenethyloxy. These substituents may be further substituted.

Specific examples of the "aryloxy" in the "substituted or unsubstituted aryloxy" represented by R1 to R10 or Ar1 to Ar5 in general formulae (1) to (3) include phenoxy, biphenylyloxy, terphenylyloxy, naphthyloxy, anthryloxy, phenanthryloxy, fluorenyloxy, indenyloxy, and pyrenyloxy.

Specific examples of the "substituent" in the "substituted aryloxy" represented by R1 to R10 or Ar1 to Ar5 in general formulae (1) to (3) include a fluorine atom, a chlorine atom, cyano, trifluoromethyl, nitro, linear or branched alkyl of 1 to 6 carbon atoms, cycloalkyl of 5 to carbon atoms, linear or branched alkyloxy of 1 to 6 carbon atoms, cycloalkyloxy of 5 to 10 carbon atoms, phenyl, naphthyl, anthryl, styryl, phenoxy, tolyloxy, benzyloxy, and phenethyloxy. These substituents may be further substituted.

Specific examples of the "divalent group of an aromatic hydrocarbon", the "divalent group of an aromatic heterocyclic ring", or the "divalent group of a condensed polycyclic aromatic" in the "divalent group of a substituted or unsubstituted aromatic hydrocarbon", the "divalent group of a substituted or unsubstituted aromatic heterocyclic ring", or the "divalent group of a substituted or unsubstituted condensed polycyclic aromatic" represented by B or C in general formulae (2) to (3) include phenylene, biphenylene, terphenylene, tetrakisphenylene, naphthylene, anthrylene, phenanthrylene, fluorenylene, phenanthrolylene, indenylene, pyrenylene, acenaphthenylene, fluoranthenylene, triphenylenylene, pyridinylene, pyrimidinylene, quinolylene, isoquinolylene, indolylene, carbazolylene, quinoxalylene, benzoimidazolylene, pyrazolylene, naphthyridinylene, phenanthrolinylene, acridinylene, thienylene, benzothienylene, and dibenzothienylene.

Specific examples of the "substituent" in the "divalent group of a substituted aromatic hydrocarbon", the "divalent group of a substituted aromatic heterocyclic ring", or the "divalent group of a substituted condensed polycyclic aromatic" represented by B or C in general formulae (2) to (3) include a fluorine atom, a chlorine atom, cyano, trifluoromethyl, nitro, linear or branched alkyl of 1 to 6 carbon atoms, cycloalkyl of 5 to 10 carbon atoms, linear or branched alkenyl of 2 to 6 carbon atoms, linear or branched alkyloxy of 1 to 6 carbon atoms, cycloalkyloxy of 5 to 10 carbon atoms, phenyl, naphthyl, anthryl, styryl, phenoxy, tolyloxy, benzyloxy, and phenethyloxy. These substituents may be further substituted.

Specific examples of the "linear or branched alkyl of 1 to 6 carbon atoms", or the "linear or branched alkenyl of 2 to 6 carbon atoms" represented by R11 to R22 in general formula (4) include methyl, ethyl, n-propyl, isopropyl, n-butyl, isobutyl, tert-butyl, n-pentyl, isopentyl, neopentyl, n-hexyl, vinyl, allyl, isopropenyl, and 2-butenyl.

Specific examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by R11 to R22 in general formula (4) include phenyl, biphenylyl, terphenylyl, tetrakisphenyl, styryl, naphthyl, anthryl, acenaphthenyl, fluorenyl, phenanthryl, indenyl, pyrenyl, pyridyl, pyrimidyl, furanyl, pyranyl, thienyl, quinolyl, isoquinolyl, benzofuranyl, benzothienyl, indolyl, carbazolyl, benzooxazolyl, benzothiazolyl, quinoxalyl, benzoimidazolyl, pyrazolyl, dibenzofuranyl, dibenzothienyl, naphthyridinyl, phenanthrolinyl, and acridinyl.

Specific examples of the "substituent" in the "substituted aromatic hydrocarbon group", the "substituted aromatic heterocyclic group", or the "substituted condensed polycyclic aromatic group" represented by R11 to R22 in general formula (4) include a fluorine atom, a chlorine atom, trifluoromethyl, linear or branched alkyl of 1 to 6 carbon atoms, phenyl, biphenylyl, terphenylyl, tetrakisphenyl, styryl, naphthyl, fluorenyl, phenanthryl, indenyl, and pyrenyl. These substituents may be further substituted.

Among the compounds of the general formula (1) having a carbazole ring structure, the compounds of the following general formula (1') having a carbazole ring structure with n=0, and the compounds of the following general formula (1") having a carbazole ring structure with n=1 are preferably used for an organic EL device.

[Chemical Formula 15]

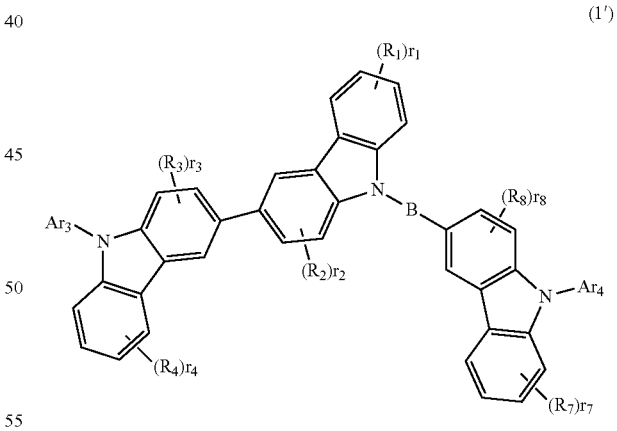

(1')

In the formula, R1, R2, R3, R4, R7, and R8 may be the same or different, and represent a fluorine atom, a chlorine atom, cyano, trifluoromethyl, nitro, linear or branched alkyl of 1 to 6 carbon atoms, cycloalkyl of 5 to 10 carbon atoms, linear or branched alkyloxy of 1 to 6 carbon atoms, cycloalkyloxy of 5 to 10 carbon atoms, a substituted or unsubstituted aromatic hydrocarbon group, a substituted or unsubstituted aromatic heterocyclic group, a substituted or unsubstituted condensed polycyclic aromatic group, or substituted or unsubstituted aryloxy. r1, r4, and r7 represent 0 or an integer of 1 to 4. r2, r3, and r8 represent 0 or an integer of 1 to 3. B represents a divalent group of a substituted or unsubstituted aromatic hydrocarbon group, a divalent group of a substituted or unsubstituted aromatic heterocyclic ring, or a divalent group of a substituted or unsubstituted condensed polycyclic aromatic. Ar3 and Ar4 may be the same or different, and represent a substituted or unsubstituted aromatic hydrocarbon group, a substituted or unsubstituted aromatic heterocyclic group, or a substituted or unsubstituted condensed polycyclic aromatic group.

[Chemical Formula 16]

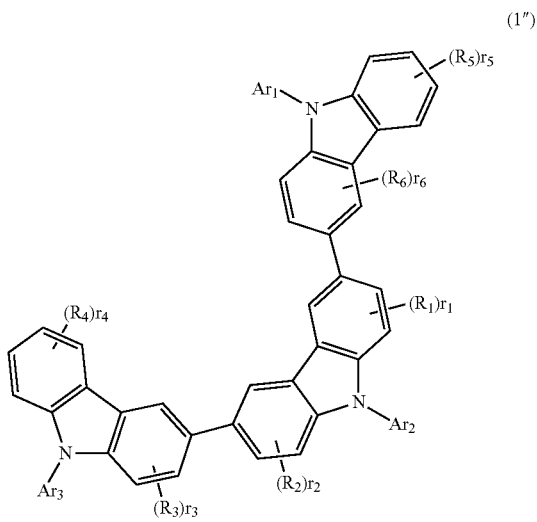

(1″)

In the formula, R1, R2, R3, R4, R5, and R6 may be the same or different, and represent a fluorine atom, a chlorine atom, cyano, trifluoromethyl, nitro, linear or branched alkyl of 1 to 6 carbon atoms, cycloalkyl of 5 to carbon atoms, linear or branched alkyloxy of 1 to 6 carbon atoms, cycloalkyloxy of 5 to 10 carbon atoms, a substituted or unsubstituted aromatic hydrocarbon group, a substituted or unsubstituted aromatic heterocyclic group, a substituted or unsubstituted condensed polycyclic aromatic group, or substituted or unsubstituted aryloxy. r4 and r5 represent 0 or an integer of 1 to 4. r1, r2, r3, and r6 represent 0 or an integer of 1 to 3. Ar1, Ar2, and Ar3 may be the same or different, and represent a substituted or unsubstituted aromatic hydrocarbon group, a substituted or unsubstituted aromatic heterocyclic group, or a substituted or unsubstituted condensed polycyclic aromatic group.

The compounds of general formula (1) having a carbazole ring structure used for the organic EL device of the present invention are highly capable of confining triplet excitons, and have superior electron blocking ability and heat resistance, and a stable thin-film state.

The compounds of general formula (1) having a carbazole ring structure used for the organic EL device of the present invention may be used as a constituent material of the hole injection layer and/or hole transport layer of the organic EL device, particularly a phosphorescent organic EL device. With the compounds having high hole injectability, high mobility, high T₁ value, and high electron stability, the triplet excitons generated in the light emitting layer containing the phosphorescent light-emitting material can be confined, and the probability of hole-electron recombination can be improved. This improves the luminous efficiency, and lowers driving voltage and thus improves the durability of the organic EL device.

The compounds of general formula (1) having a carbazole ring structure used for the organic EL device of the present invention also may be used as a constituent material of the electron blocking layer of the organic EL device, particularly a phosphorescent organic EL device. With the material having high triplet exciton confining capability and excellent hole transportability with high stability in the thin-film state, the driving voltage lowers and the current resistance improves while maintaining high luminous efficiency. As a result, the maximum emission luminance of the organic EL device improves.

The compounds of general formula (1) having a carbazole ring structure used for the organic EL device of the present invention also may be used as a constituent material of the light emitting layer of the organic EL device, particularly a phosphorescent organic EL device. The compounds have excellent hole transportability and a wide band gap, and can thus be used as the host material of the light emitting layer in order to form the light emitting layer by carrying a phosphorescent material called a dopant. In this way, an organic EL device can be realized that has a low driving voltage and improved luminous efficiency.

The organic EL device of the present invention uses the compound having a carbazole ring structure, wherein the compound has high hole mobility and excellent triplet exciton confining capability while having a stable thin-film state. In this way, high efficiency and high durability are realized.

Advantage of the Invention

The compound having a carbazole ring structure used for the organic EL device of the present invention is useful as a constituent material of the hole injection layer and the hole transport layer of the organic EL device, particularly a phosphorescent organic EL device. The compound has excellent triplet exciton confining capability, and excels in heat resistance while having a stable thin-film state. The organic EL device of the present invention has high luminous efficiency and high power efficiency, and can thus lower the actual driving voltage of the device. Further, the turn on voltage can be lowered to improve durability.

MODE FOR CARRYING OUT THE INVENTION

Figure 1:
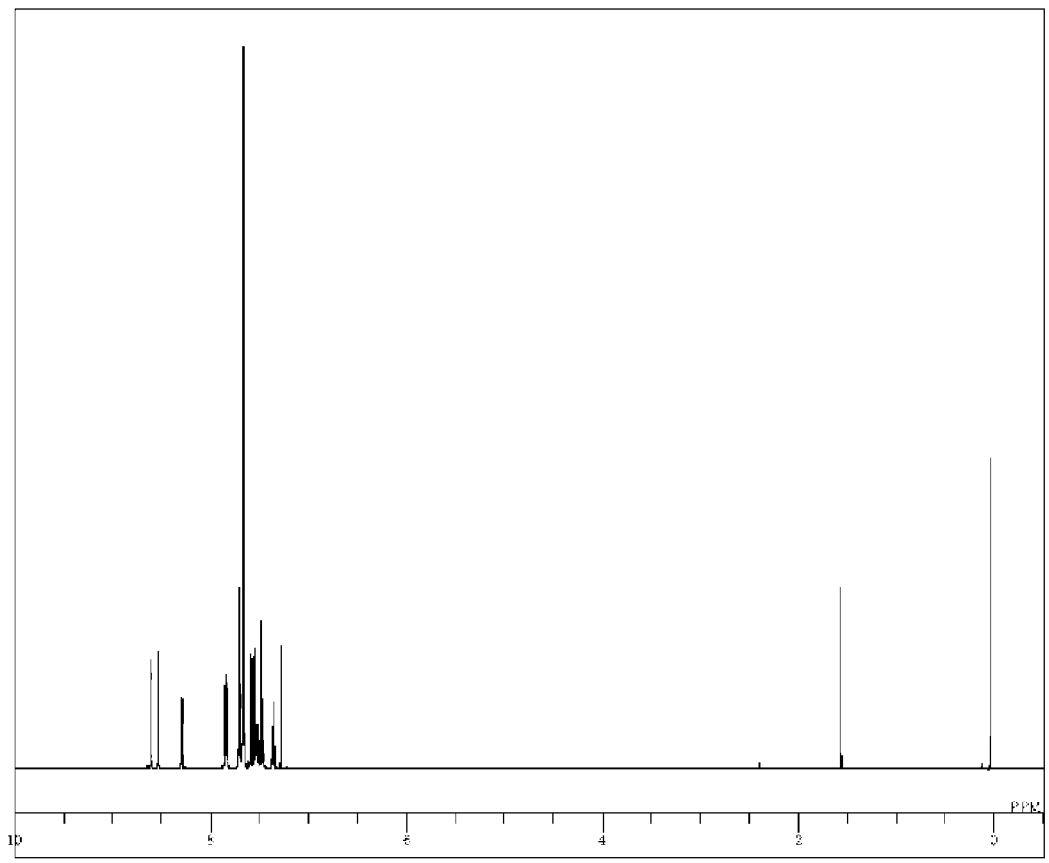
FIG. 1 is a ¹H-NMR chart of the compound of Example 1 of the present invention (Compound 5).

The compounds having a carbazole ring structure used in the present invention may be synthesized by using known methods (see, for example, Patent Document 3), or by using, for example, the following method. First, a monobromocarbazole such as 3-bromo-9-arylcarbazole, or a dibromocarbazole such as 3,6-dibromo-9-arylcarbazole is synthesized by the bromination of a carbazole substituted with an aryl group at the corresponding ninth position, using, for example, N-bromosuccinimide (see, for example, Non-Patent Document 6). The boronic acid or borate synthesized by the reaction of the resulting monobromocarbazole with a compound such as pinacolborane or bis(pinacolato)diboron (see, for example, Non-Patent Document 7) can then be reacted with dibromocarbazole or monobromocarbazole in a cross-coupling reaction such as Suzuki coupling (see, for example, Non-Patent Document 8) to synthesize bis(N-aryl-9'H-carbazol-3'-yl)-9-aryl-9H-carbazole or (N-aryl-9'H-carbazol-3'-yl)-9H-carbazole. The (N-aryl-9'H-carbazol-3'-yl)-9-halogenoaryl-carbazole obtained by the condensation reaction (such as Ullmann reaction) of the (N-aryl-9'H-carbazol-3'-yl)-9H-carbazole with various dihalogenoarylenes can be reacted with 3-boronic acid or borate of 9-arylcarbazole in a cross-coupling reaction such as Suzuki coupling (see, for example, Non-Patent Document 8) to synthesize a compound having a carbazole ring structure.

The following presents specific examples of preferred compounds among the compounds of general formula (1) having a carbazole ring structure. The present invention, however, is not restricted to these compounds.

[Chemical Formula 17]

(Compound 5)

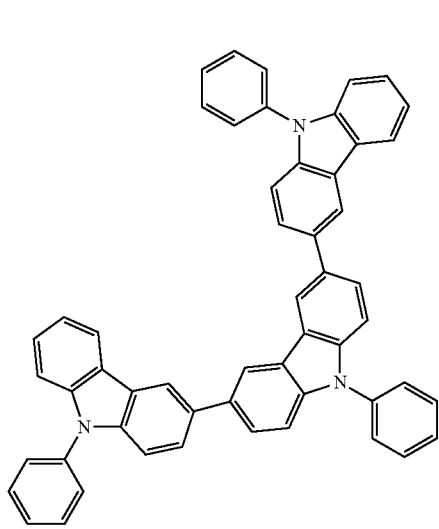

[Chemical Formula 18]

(Compound 6)

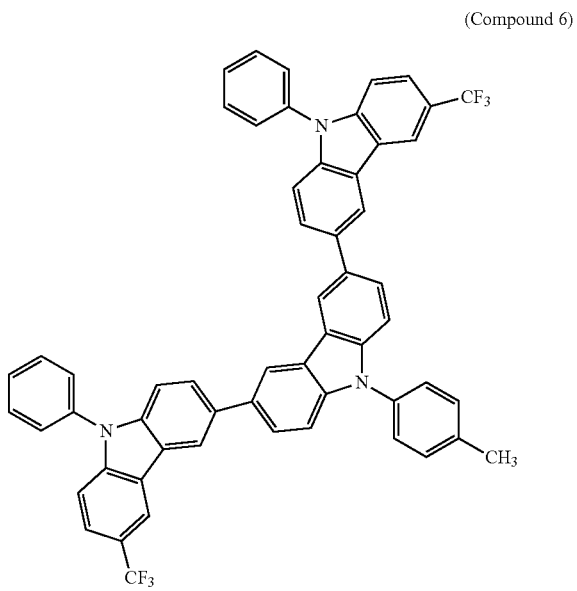

[Chemical Formula 19]

(Compound 7)

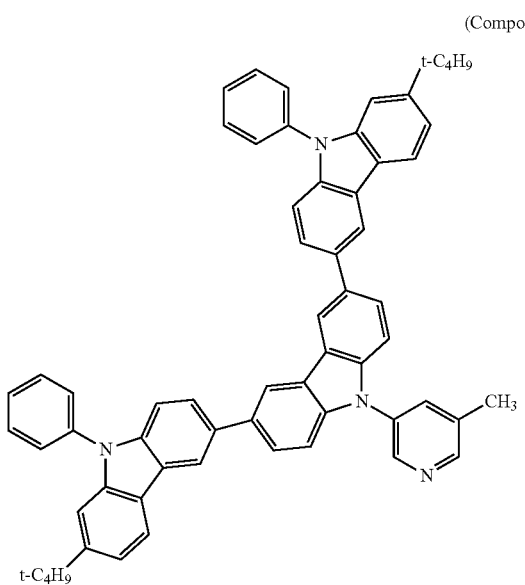

[Chemical Formula 20]

(Compound 8)

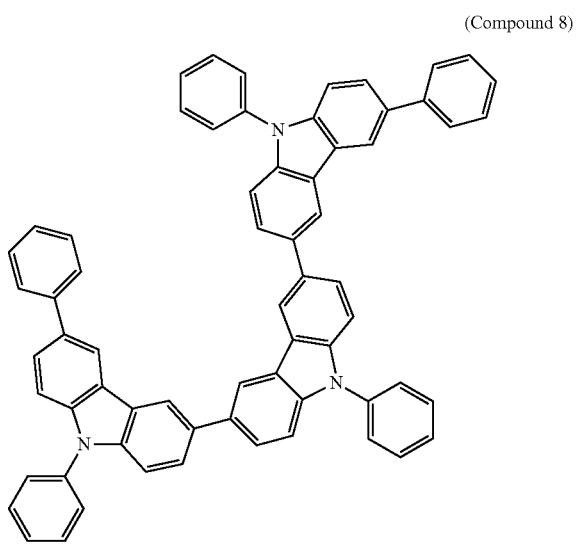

[Chemical Formula 21]
(Compound 9)
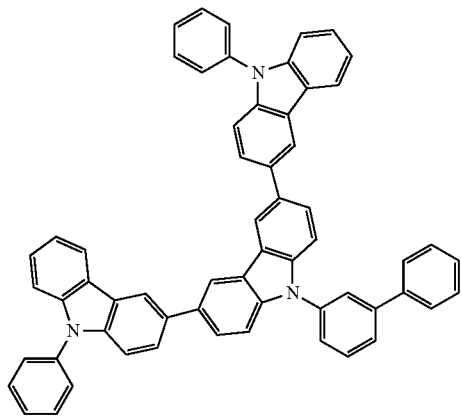
[Chemical Formula 22]
(Compound 10)
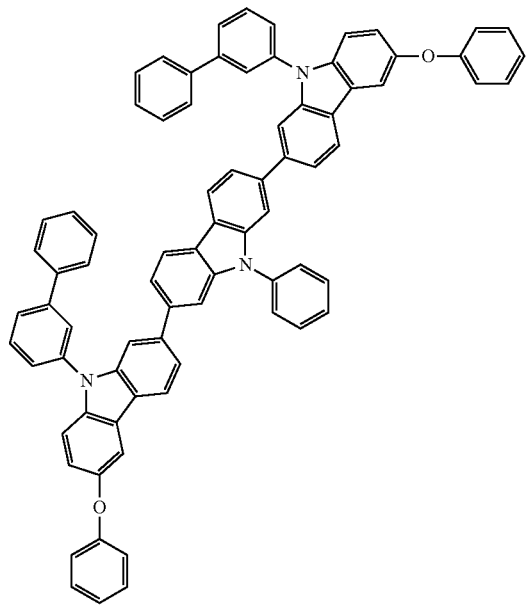
[Chemical Formula 23]
(Compound 11)
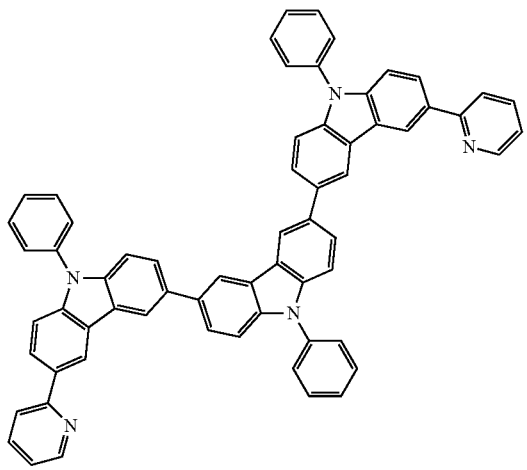
[Chemical Formula 24]
(Compound 12)
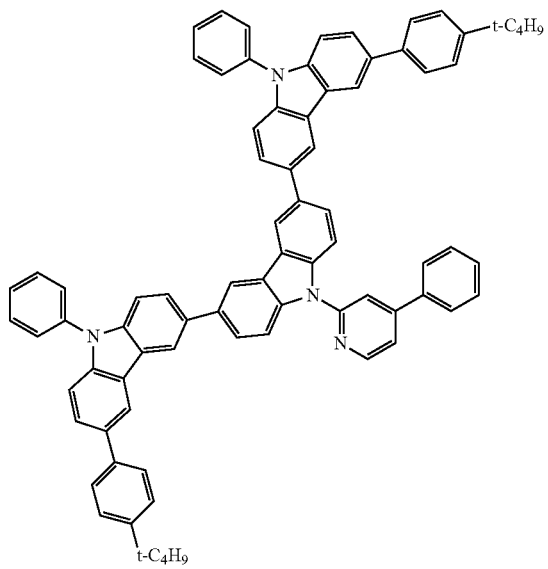

-continued
[Chemical Formula 25]
(Compound 13)
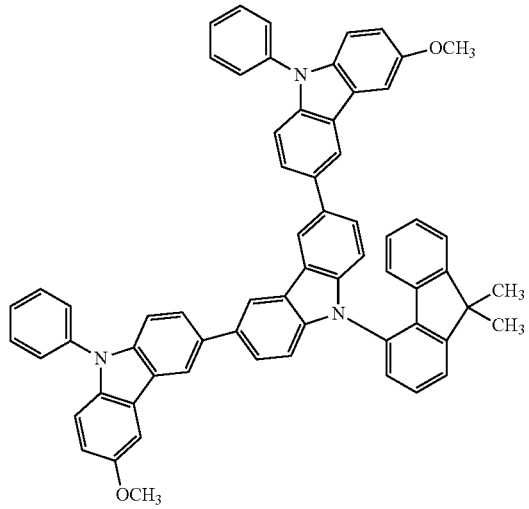
[Chemical Formula 26]
(Compound 14)
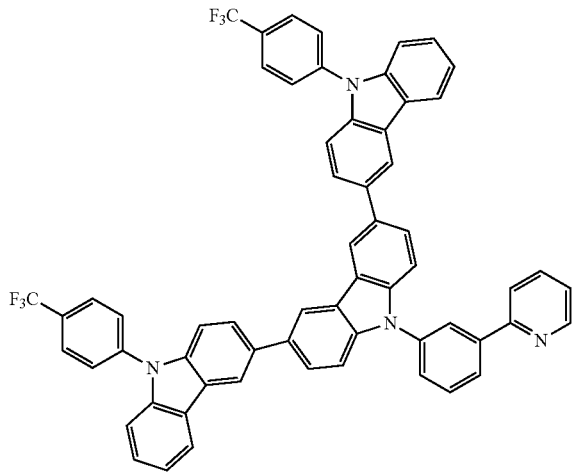
[Chemical Formula 27]
(Compound 15)
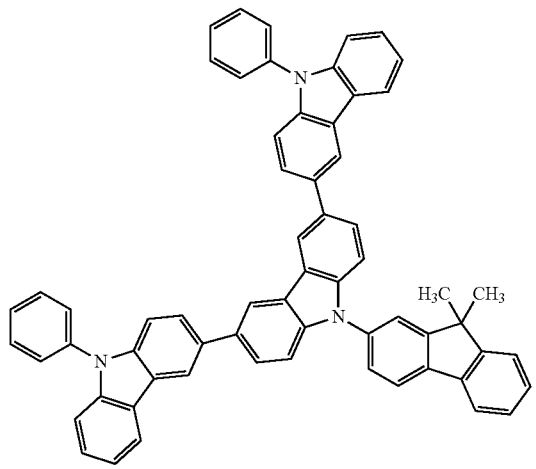
[Chemical Formula 28]
(Compound 16)
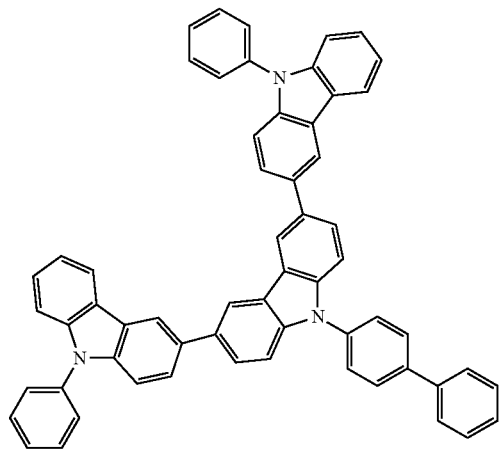
[Chemical Formula 29]
(Compound 17)
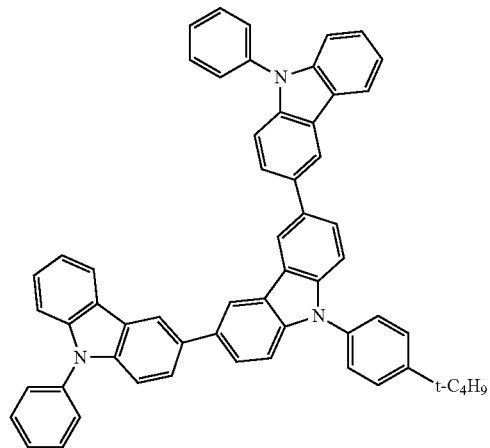
[Chemical Formula 30]
(Compound 18)
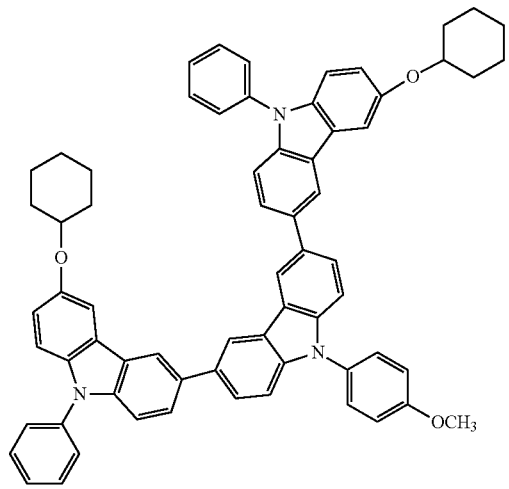

[Chemical Formula 31]
(Compound 19)
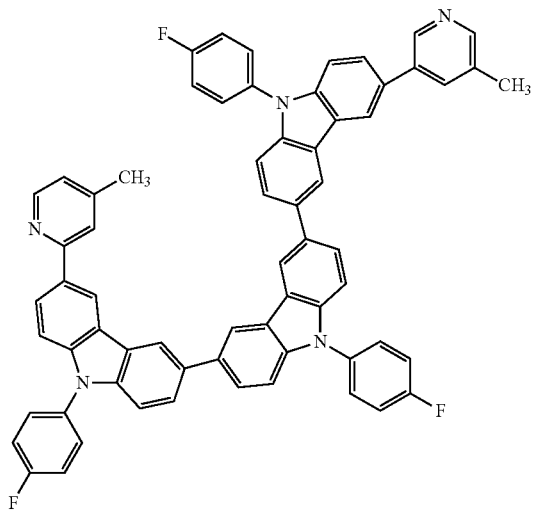
[Chemical Formula 32]
(Compound 20)
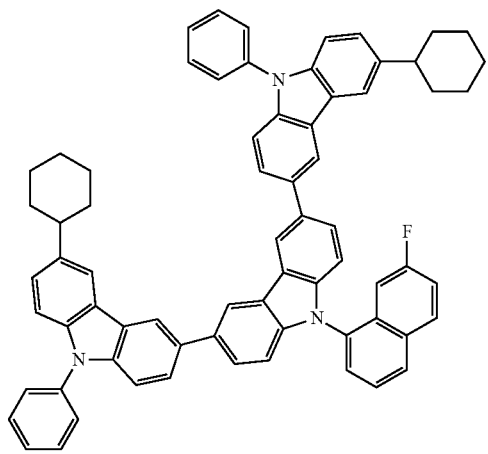
[Chemical Formula 33]
(Compound 21)
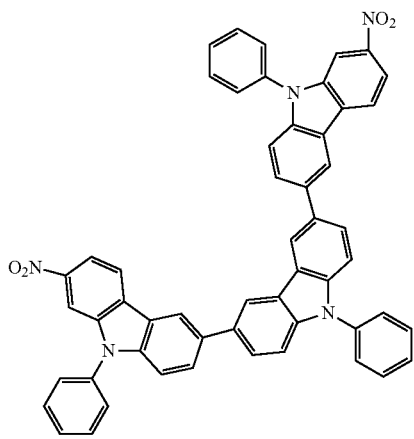
[Chemical Formula 34]
(Compound 22)
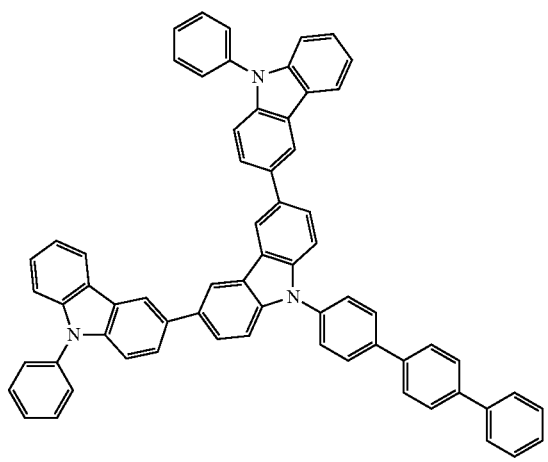

[Chemical Formula 35]
(Compound 23)
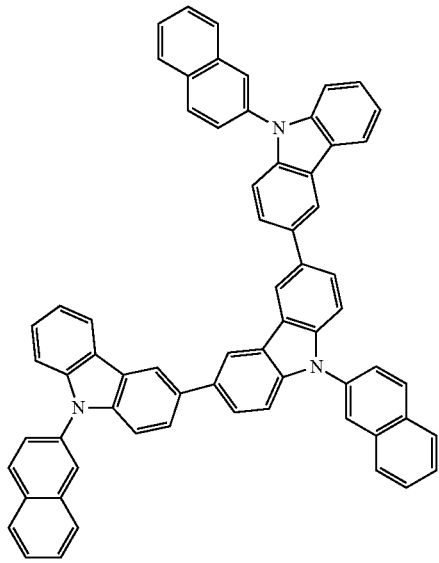
[Chemical Formula 36]
(Compound 24)
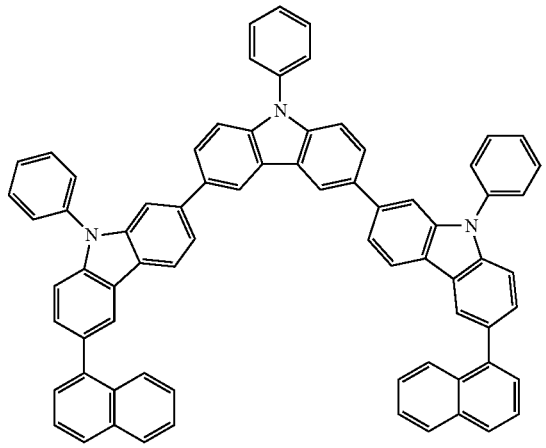
[Chemical Formula 37]
(Compound 25)
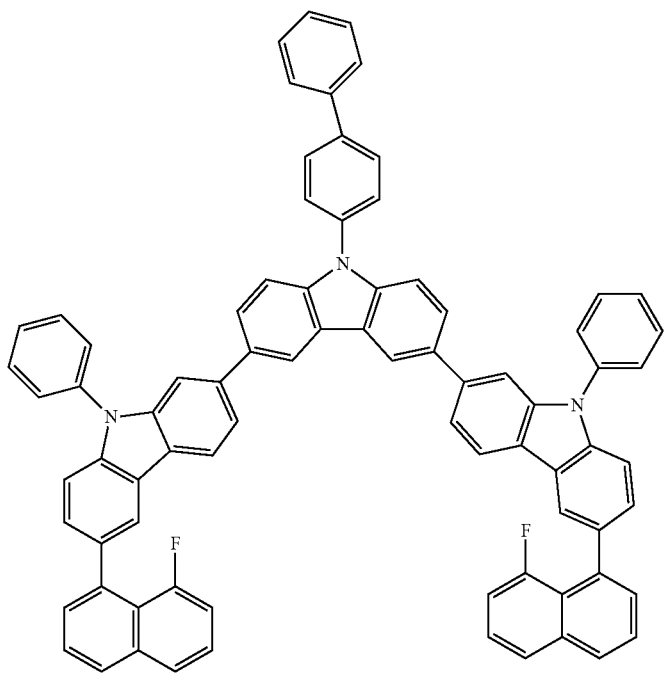

[Chemical Formula 38]
(Compound 26)
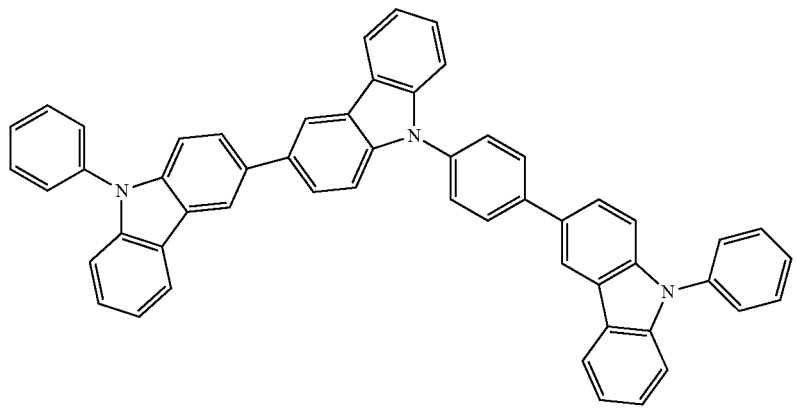
[Chemical Formula 39]
(Compound 27)
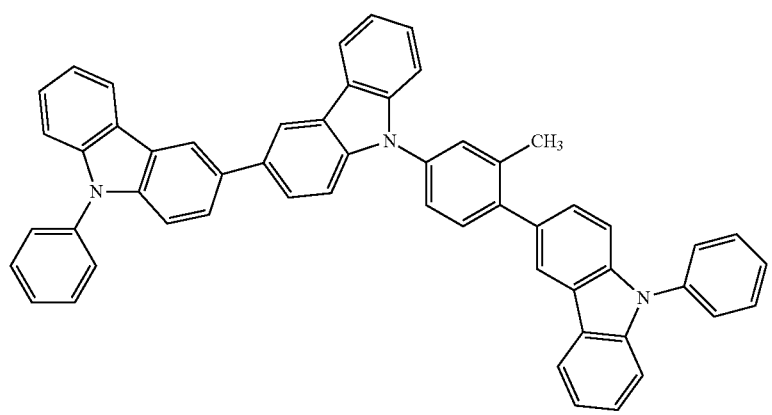
[Chemical Formula 40]
(Compound 28)
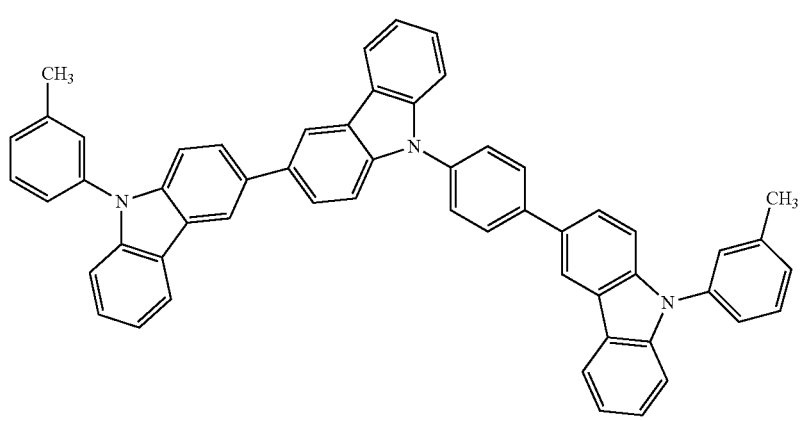

[Chemical Formula 41]
(Compound 29)
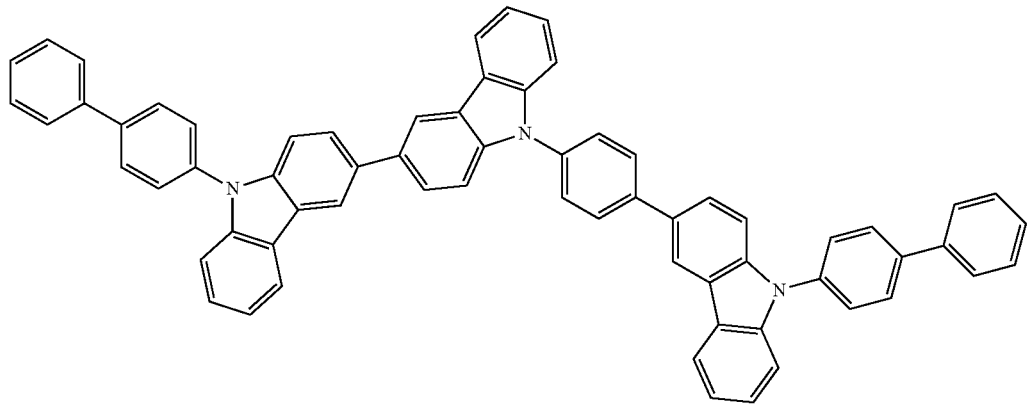
[Chemical Formula 42]
(Compound 30)
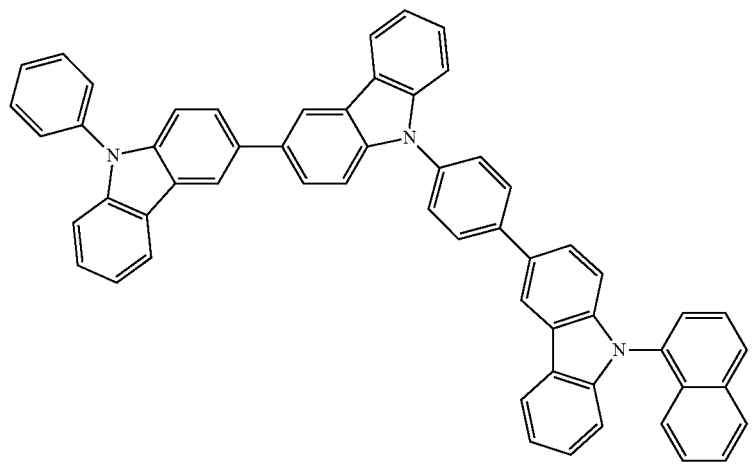
[Chemical Formula 43]
(Compound 31)
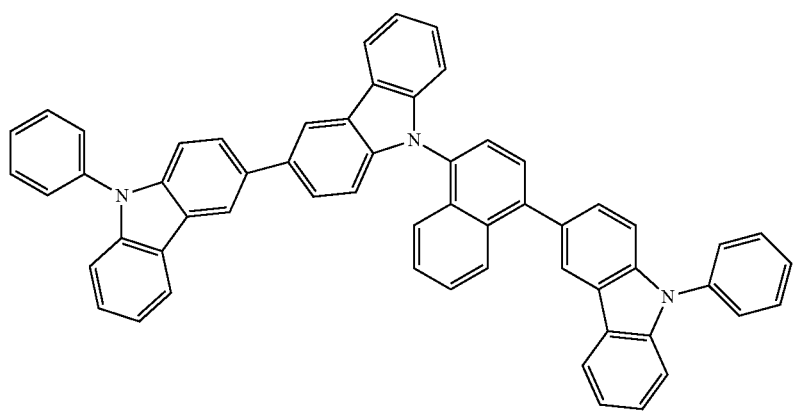

[Chemical Formula 44]
(Compound 32)
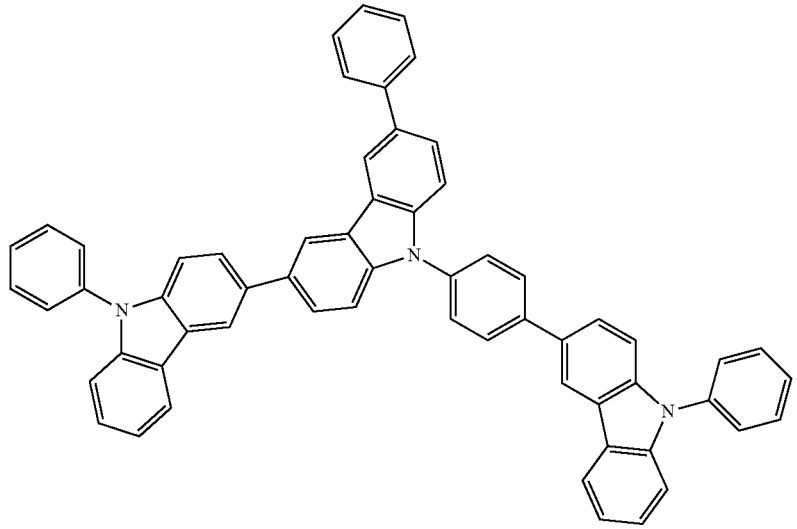
[Chemical Formula 45]
(Compound 33)
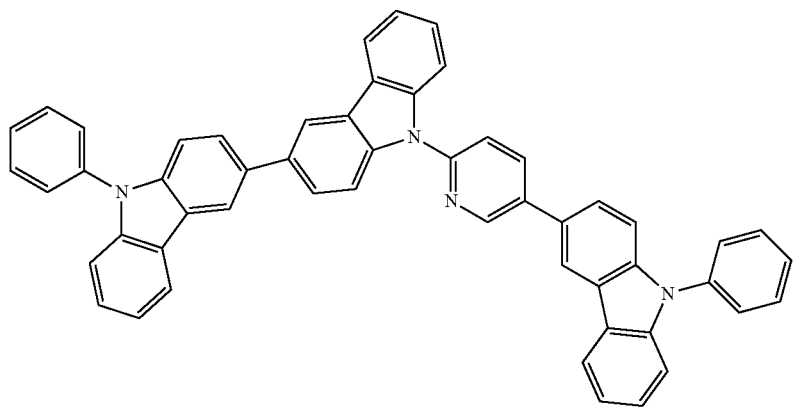
[Chemical Formula 46]
(Compound 34)
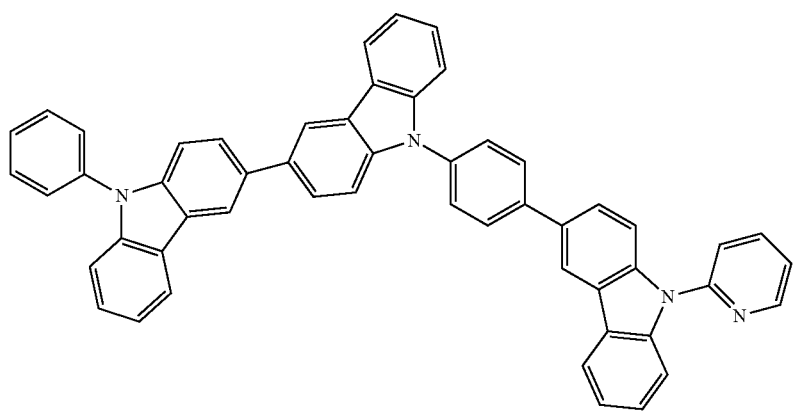

[Chemical Formula 47]
(Compound 35)
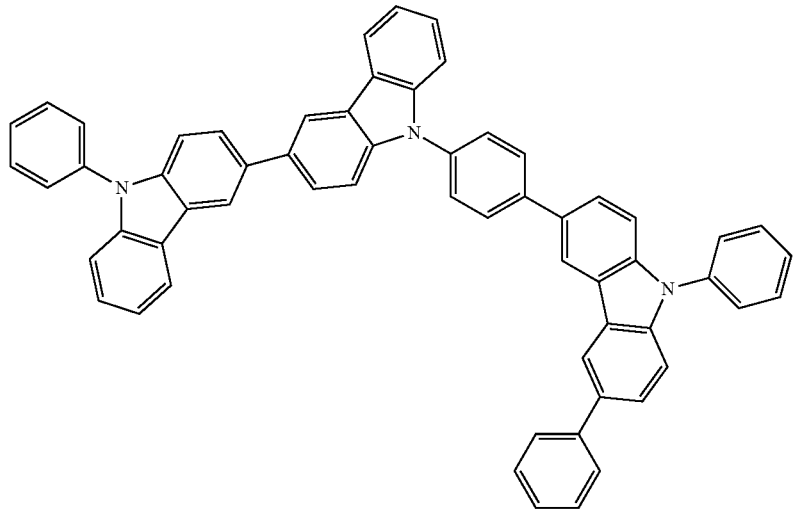
[Chemical Formula 48]
(Compound 36)
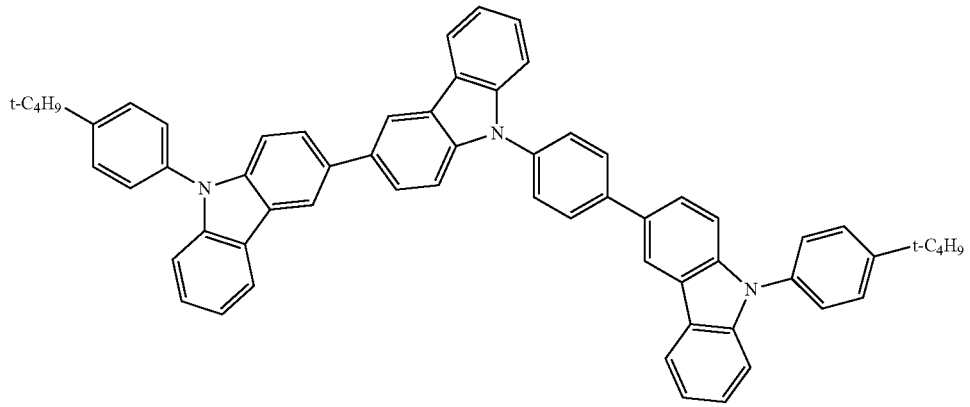
[Chemical Formula 49]
(Compound 37)
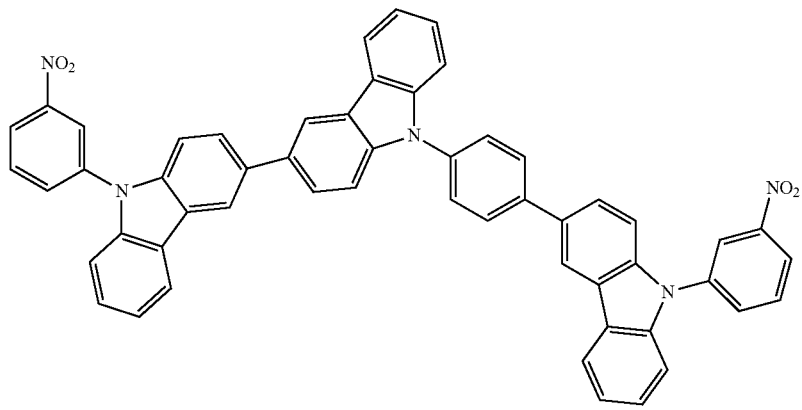

[Chemical Formula 50]
(Compound 38)
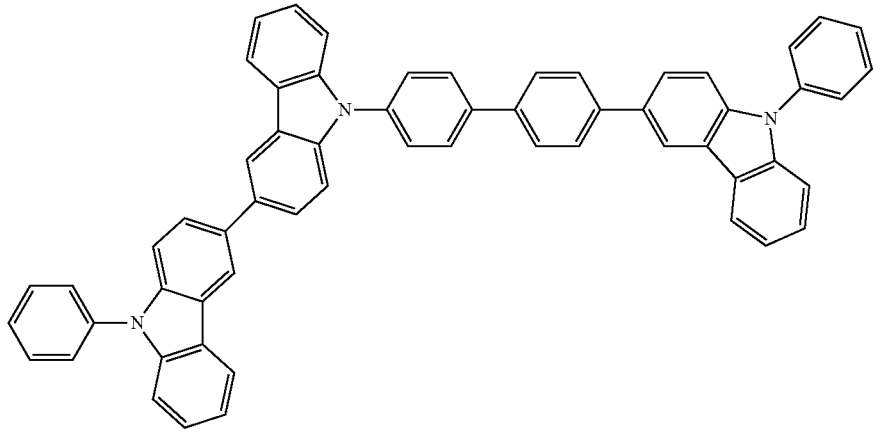
[Chemical Formula 51]
(Compound 39)
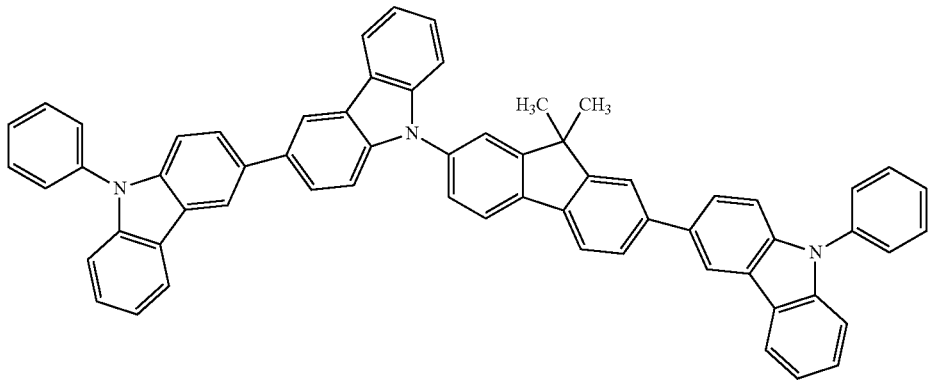
[Chemical Formula 52]
(Compound 40)
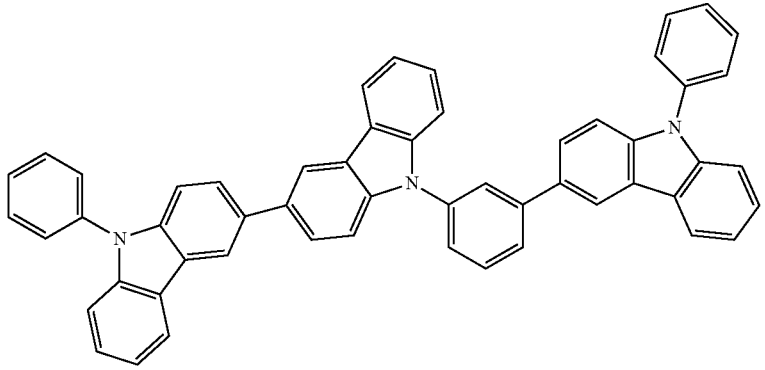

[Chemical Formula 53]
(Compound 41)
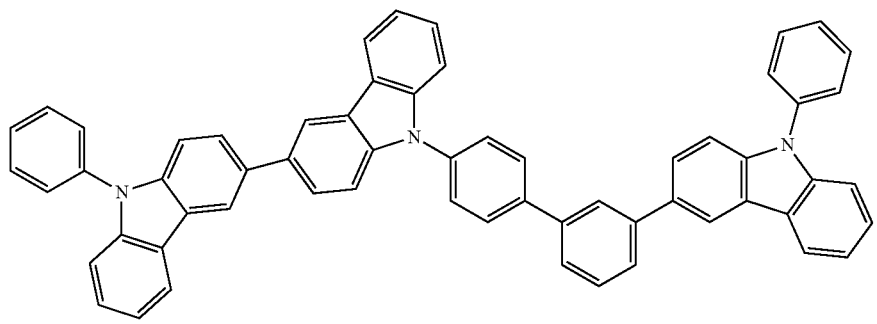
[Chemical Formula 54]
(Compound 42)
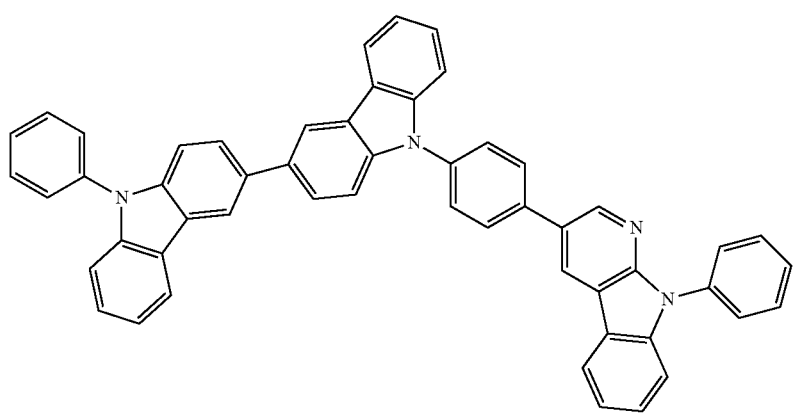
[Chemical Formula 55]
(Compound 43)
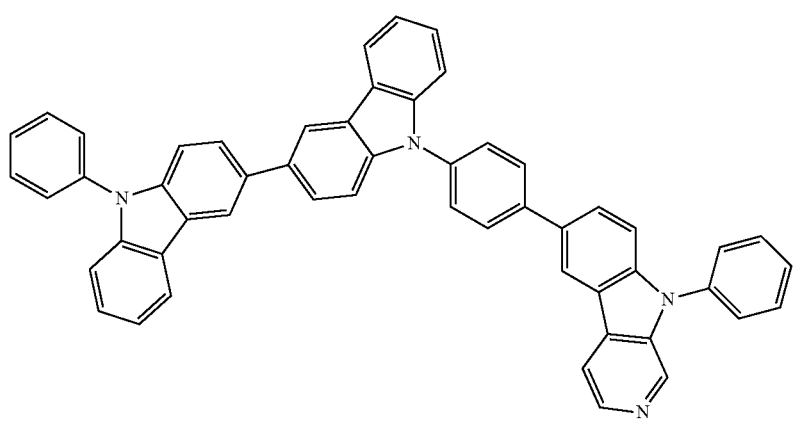

[Chemical Formula 56]
(Compound 44)
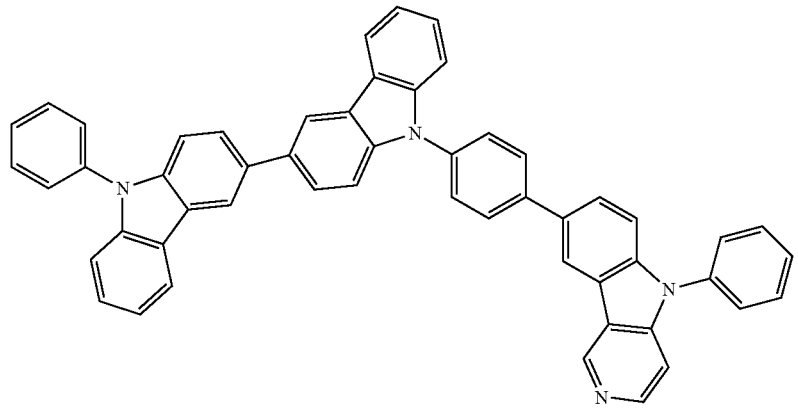
[Chemical Formula 57]
(Compound 45)
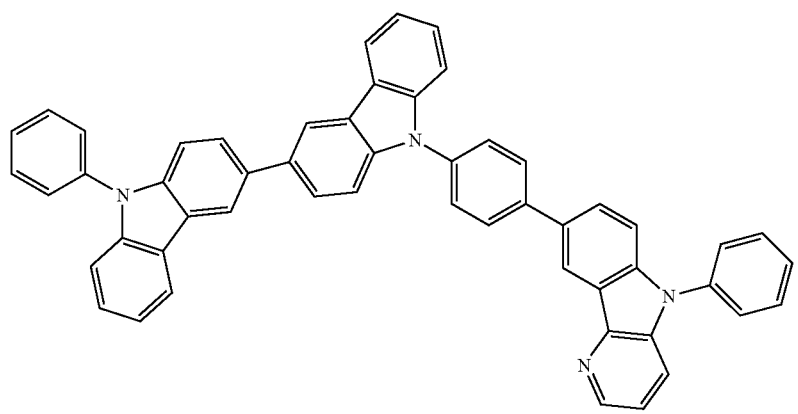
[Chemical Formula 58]
(Compound 46)
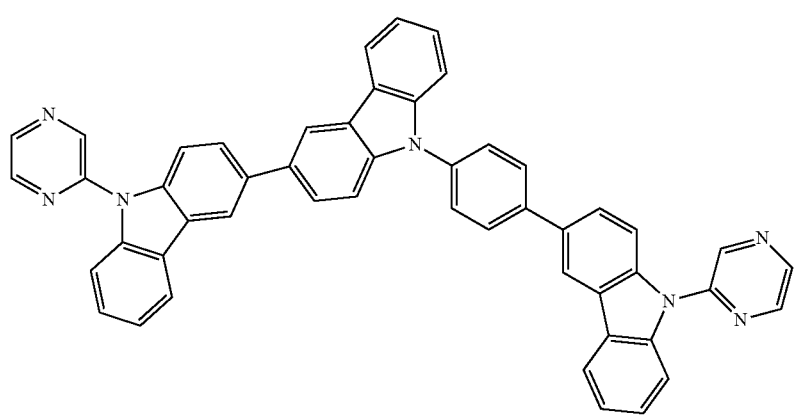

[Chemical Formula 59]
(Compound 47)
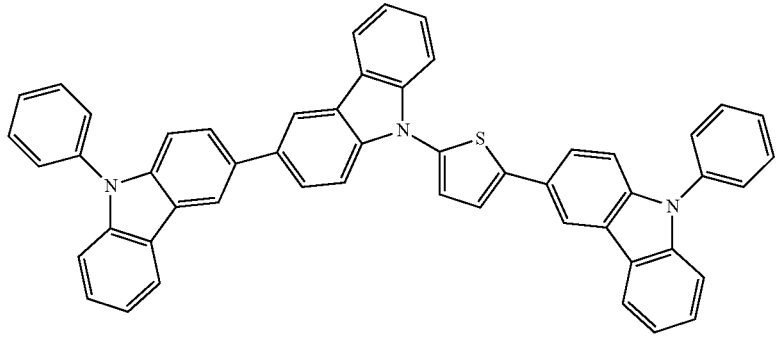
[Chemical Formula 60]
(Compound 48)
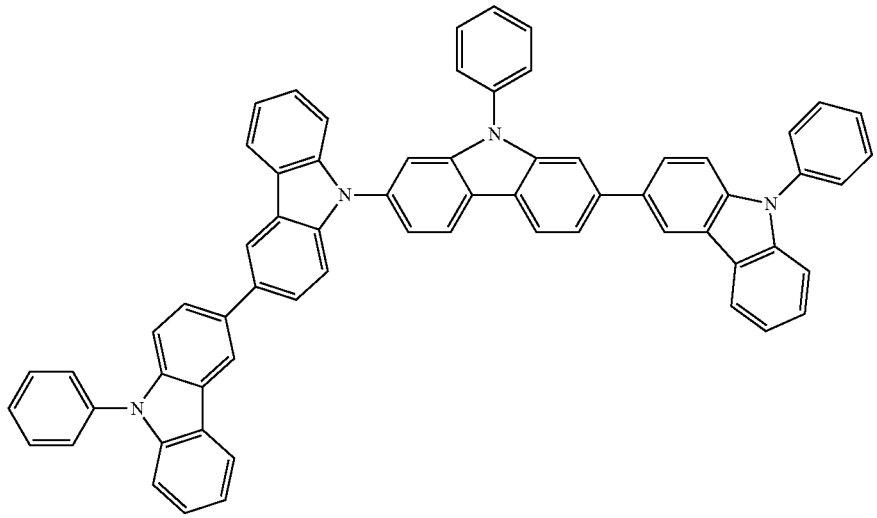
[Chemical Formula 61]
(Compound 49)
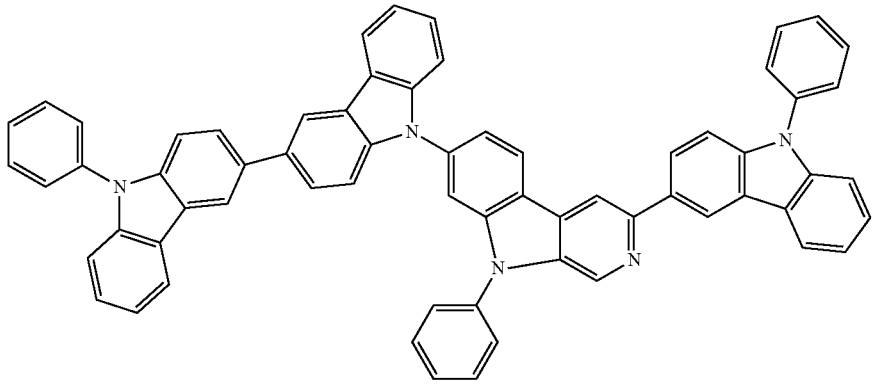

-continued
[Chemical Formula 62]
(Compound 50)
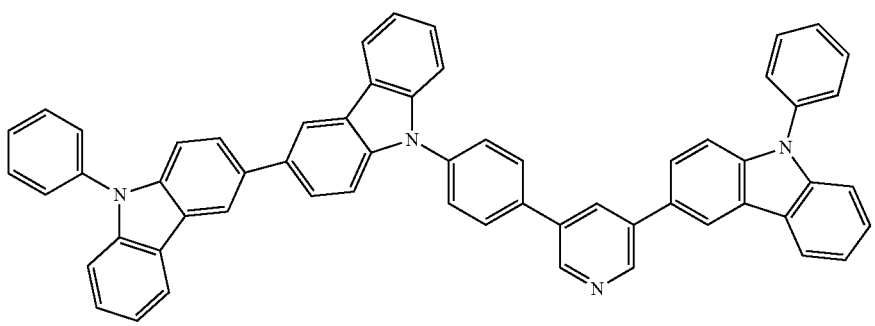
[Chemical Formula 63]
(Compound 51)
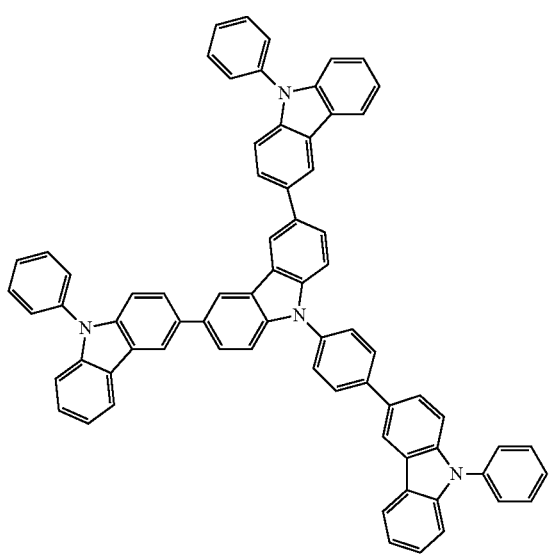
[Chemical Formula 64]
(Compound 52)
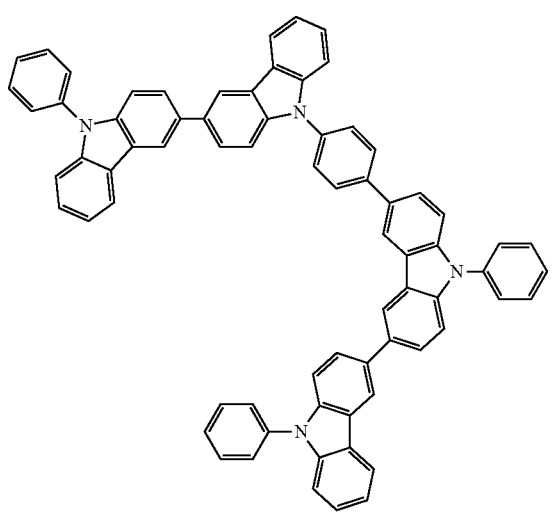
[Chemical Formula 65]
(Compound 53)
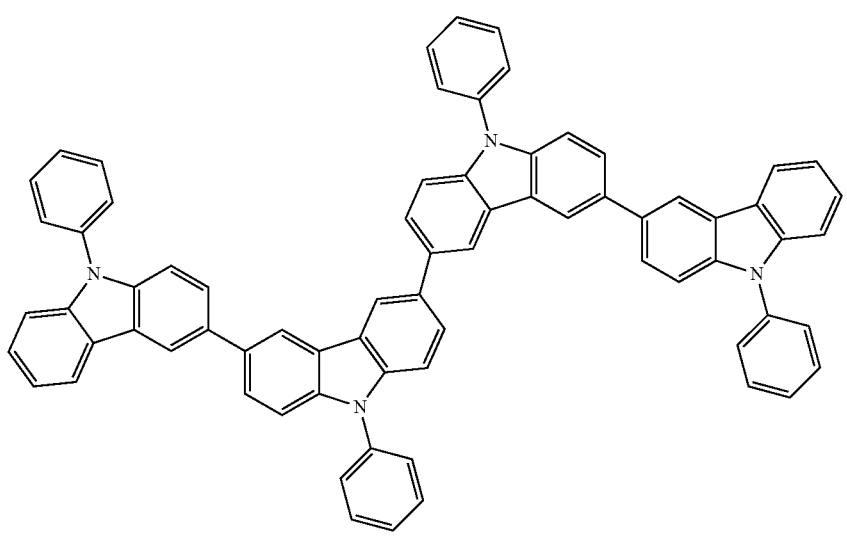

These compounds were purified by methods such as column chromatography, adsorption using, for example, a silica gel, activated carbon, or activated clay, and recrystallization or crystallization using a solvent. The compounds were identified by NMR analysis. Glass transition point (Tg) and work function were taken for the measurement of physical properties. Glass transition point (Tg) can be used as an index of stability in the thin-film state, and the work function as an index of hole transportability.

The glass transition point (Tg) was measured using a powder, using a high-sensitive differential scanning calorimeter DSC3100S produced by Bruker AXS.

For the measurement of work function, a 100 nm-thick thin film was fabricated on an ITO substrate, and an atmosphere photoelectron spectrometer AC-3 produced by Riken Keiki Co., Ltd. was used.

The $T_1$ values of these compounds can be calculated from the measured phosphorescence spectrum. The phosphorescence spectrum can be measured using a commercially available spectrophotometer. Typically, the phosphorescence spectrum is measured by shining excitation light under low temperature on the compound dissolved in a solvent (see, for example, Non-Patent Document 9), or by shining excitation light under low temperature on the compound formed into a thin film by being vapor deposited on a silicon substrate (see, for example, Patent Document 6). $T_1$ can be calculated by conversion into a light energy value according to the equation below from the wavelength of the first peak on the shorter wavelength side of the phosphorescence spectrum, or from the wavelength at the rise of the spectrum on the shorter wavelength side. $T_1$ is used as an index of triplet exciton confinement by the phosphorescent material.

$$E(\text{eV}) = hc/\lambda \quad \text{[Equation 1]}$$

In the equation, E represents the light energy value, h the Planck's constant ($6.63 \times 10^{-34}$ Js), c the speed of light ($3.00 \times 10^8$ m/s), and $\lambda$ the wavelength (nm) at the rise of the phosphorescence spectrum on the shorter wavelength side. 1 eV=$1.60 \times 10^{-19}$ J.

The organic EL device of the present invention may have a structure including an anode, a hole injection layer, a hole transport layer, an electron blocking layer, a light emitting layer, a hole blocking layer, an electron transport layer, and a cathode successively formed on a substrate, optionally with an electron injection layer between the electron transport layer and the cathode. Some of the organic layers in this multilayer structure may be omitted.

Each of the light emitting layer, the hole transport layer, and the electron transport layer may have a laminate structure of two or more layers.

Electrode materials with a large work function, such as ITO and gold, are used as the anode of the organic EL device of the present invention. The hole injection layer of the organic EL device of the present invention may be made of a material, the examples of which include porphyrin compounds as represented by copper phthalocyanine, starburst-type triphenylamine derivatives, triphenylamine trimers and tetramers such as an arylamine compound of a structure in which three or more triphenylamine structures are joined to each other within the molecule via a single bond or a divalent group that does not contain a heteroatom, accepting heterocyclic compounds such as hexacyano azatriphenylene, and coating-type polymer materials, in addition to the compounds of general formula (1) having a carbazole ring structure of the present invention. These materials may be formed into a thin film by using a vapor deposition method, or other known methods such as spin coating and an inkjet method.

Examples of the material used for the hole transport layer of the organic EL device of the present invention include benzidine derivatives (such as TPD, α-NPD, and N,N,N',N'-tetrabiphenylylbenzidine), TAPC, and various triphenylamine trimers and tetramers, in addition to the compounds of general formula (1) having a carbazole ring structure of the present invention. These may be individually deposited for film forming, or may be used as a single layer deposited as a mixture with other materials, or as a laminate of individually deposited layers, a laminate of layers deposited as a mixture, or a laminate of layers deposited by being mixed with an individually deposited layer. Examples of the material used for the hole injection/transport layer include coating-type polymer materials such as poly(3,4-ethylenedioxythiophene) (hereinafter, simply "PEDOT")/poly(styrene sulfonate) (hereinafter, simply "PSS"). These materials may be formed into a thin-film by using a vapor deposition method, or other known methods such as spin coating and an inkjet method.

Further, the hole injection layer or the hole transport layer may be one obtained by the P-doping of material such as trisbromophenylamine hexachloroantimony in the material commonly used for these layers. Further, for example, polymer compounds having a TPD structure as a part of the compound structure also may be used.

Examples of the material used for the electron blocking layer of the organic EL device of the present invention include compounds having an electron blocking effect, including, for example, carbazole derivatives such as 4,4',4"-tri(N-carbazolyl)triphenylamine (hereinafter, simply "TCTA"), 9,9-bis[4-(carbazol-9-yl)phenyl]fluorene, 1,3-bis(carbazol-9-yl)benzene (hereinafter, simply "mCP"), and 2,2-bis(4-carbazol-9-ylphenyl)adamantane (hereinafter, simply "Ad-Cz"); and compounds having a triphenylsilyl group and a triarylamine structure, as represented by 9-[4-(carbazol-9-yl)phenyl]-9-[4-(triphenylsilyl)phenyl]-9H-fluorene, in addition to the compounds of general formula (1) having a carbazole ring structure of the present invention. These may be individually deposited for film forming, or may be used as a single layer deposited as a mixture with other materials, or as a laminate of individually deposited layers, a laminate of layers deposited as a mixture, or a laminate of layers deposited by being mixed with an individually deposited layer. These materials may be formed into a thin-film by using a vapor deposition method, or other known methods such as spin coating and an inkjet method.

Examples of the material used for the light emitting layer of the organic EL device of the present invention include various metal complexes, anthracene derivatives, bis(styryl)benzene derivatives, pyrene derivatives, oxazole derivatives, and polyparaphenylene vinylene derivatives, in addition to quinolinol derivative metal complexes such as $Alq_3$. Further, the light emitting layer may be configured from a host material and a dopant material. Examples of the host material include thiazole derivatives, benzimidazole derivatives, and polydialkyl fluorene derivatives, in addition to the foregoing light-emitting materials, and the compounds of general formula (1) having a carbazole ring structure of the present invention. Examples of the dopant material include quinacridone, coumarin, rubrene, perylene, derivatives thereof, benzopyran derivatives, rhodamine derivatives, and aminostyryl derivatives. These may be individually deposited for film forming, or may be used as a single layer deposited as a mixture with other materials, or as a laminate of individually deposited layers, a laminate of layers deposited as a mixture, or a laminate of layers deposited by being mixed with an individually deposited layer.

Further, the light-emitting material may be phosphorescent light-emitting material. Phosphorescent materials as metal complexes of metals such as iridium and platinum may be used as the phosphorescent light-emitting material. Examples of the phosphorescent materials include green phosphorescent materials such as Ir(ppy)$_3$, blue phosphorescent materials such as FIrpic and FIr6, and red phosphorescent materials such as Btp$_2$Ir(acac). Here, the compounds of general formula (1) having a carbazole ring structure of the present invention may be used as the hole injecting and transporting host material, in addition to carbazole derivatives such as 4,4'-di(N-carbazolyl)biphenyl (hereinafter, simply "CBP"), TCTA, and mCP. Compounds such as p-bis(triphenylsilyl)benzene (hereinafter, simply "UGH2"), and 2,2',2"-(1,3,5-phenylene)-tris(1-phenyl-1H-benzimidazole) (hereinafter, simply "TPBI") represented by the following formula may be used as the electron transporting host material.

[Chemical Formula 66]

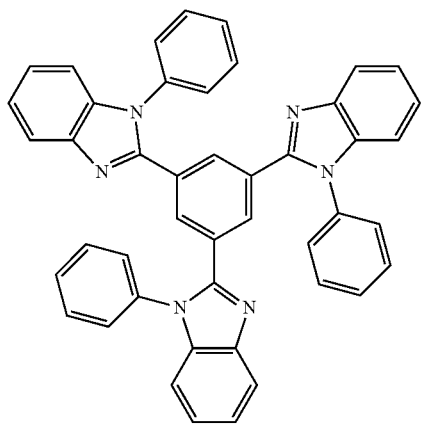

In order to avoid concentration quenching, the doping of the host material with the phosphorescent light-emitting material should preferably be made by co-evaporation in a range of 1 to 30 weight percent with respect to the whole light emitting layer.

A device including a light emitting layer fabricated with the compound of general formula (1) having a carbazole ring structure used for the organic EL device of the present invention may be produced as a laminate with an adjacently laminated light emitting layer fabricated by using a compound of a different work function as the host material (see, for example, Non-Patent Documents 10 and 11.)

These materials may be formed into a thin-film by using a vapor deposition method, or other known methods such as spin coating and an inkjet method.

The hole blocking layer of the organic EL device of the present invention may be formed by using hole blocking compounds such as various rare earth complexes, oxazole derivatives, triazole derivatives, and triazine derivatives, in addition to the metal complexes of phenanthroline derivatives such as bathocuproin (hereinafter, simply "BCP"), and the metal complexes of quinolinol derivatives such as aluminum (III) bis(2-methyl-8-quinolinate)-4-phenylphenolate (hereinafter, simply "BAlq"). These materials may also serve as the material of the electron transport layer. These may be individually deposited for film forming, or may be used as a single layer deposited as a mixture with other materials, or as a laminate of individually deposited layers, a laminate of layers deposited as a mixture, or a laminate of layers deposited by being mixed with an individually deposited layer. These materials may be formed into a thin-film by using a vapor deposition method, or other known methods such as spin coating and an inkjet method.

Examples of the material used for the electron transport layer of the organic EL device of the present invention include various metal complexes, triazole derivatives, triazine derivatives, oxadiazole derivatives, thiadiazole derivatives, carbodiimide derivatives, quinoxaline derivatives, phenanthroline derivatives, and silole derivatives, in addition to quinolinol derivative metal complexes such as Alq$_3$ and BAlq. These may be individually deposited for film forming, or may be used as a single layer deposited as a mixture with other materials, or as a laminate of individually deposited layers, a laminate of layers deposited as a mixture, or a laminate of layers deposited by being mixed with an individually deposited layer. These materials may be formed into a thin-film by using a vapor deposition method, or other known methods such as spin coating and an inkjet method.

Examples of the material used for the electron injection layer of the organic EL device of the present invention include alkali metal salts (such as lithium fluoride, and cesium fluoride), alkaline earth metal salts (such as magnesium fluoride), and metal oxides (such as aluminum oxide). However, the electron injection layer may be omitted upon preferably selecting the electron transport layer and the cathode.

The electron injection layer or the electron transport layer may be one obtained by the N-doping of metals such as cesium in the materials commonly used for these layers.

The cathode of the organic EL device of the present invention may be made of an electrode material having a low work function (such as aluminum), or an alloy of an electrode material having an even lower work function (such as a magnesium-silver alloy, a magnesium-indium alloy, or an aluminum-magnesium alloy).

The thickness of each layer in the organic EL device of the present invention is not particularly limited, and is typically from 0.1 nm to 1 μm, preferably 0.3 nm to 500 nm, because defects such as pinholes are likely to occur when the layers are thin, and because applied voltage tends to increase with thick layers.

The following describes an embodiment of the present invention in more detail based on Examples. The present invention, however, is not restricted to the following Examples.

Example 1

Synthesis of 3,6-bis(9'-phenyl-9'H-carbazol-3-yl)-9-phenyl-9H-carbazole (Compound 5)

3,6-Dibromo-9-phenyl-9H-carbazole (1.6 g), 9-phenyl-3-(4,4,5,5-tetramethyl-1,3,2-dioxabororan-2-yl)-9H-carbazole (2.4 g), toluene (20 ml), ethanol (5 ml), and a 2 M potassium carbonate aqueous solution (6 ml) were added to a nitrogen-substituted reaction vessel, and aerated with nitrogen gas for 30 minutes under ultrasonic waves. The mixture was heated after adding tetrakis(triphenylphosphine)palladium (0.23 g), and stirred at 74° C. for 4 hours. After adding toluene (80 ml), the mixture was heated, and further stirred at 70° C. for 1 hour. The mixture was then cooled to 40° C., and the insolubles were removed by filtration. The filtrate was then concentrated under reduced pressure to obtain a black crude product. Toluene (100 ml) was added to dissolve the crude product, and the solution was subjected to adsorptive purification with a silica gel (28.9 g), and concentrated under reduced pressure to obtain a yellowish white powder. The yellowish white powder was repeatedly purified twice by recrystallization using toluene/methanol to obtain a brownish white powder of 3,6-bis(9'-phenyl-9'H-carbazol-3-yl)-9-phenyl-9H-carbazole (Compound 5; 1.76 g; yield 60.9%).

The structure of the resulting brownish white powder was identified by NMR. The $^1$H-NMR measurement result is presented in FIG. 1.

1H-NMR (CDCl$_3$) detected 35 hydrogen signals, as follows. δ(ppm)=8.56 (2H), 8.49 (2H), 8.24-8.26 (2H), 7.79-7.81 (4H), 7.62-7.67 (12H), 7.43-7.55 (11H), 7.30-7.33 (2H).

Example 2

Synthesis of 9'-phenyl-9-[4-(9-phenyl-9H-carbazol-3-yl)-phenyl]-9H,9'H-[3,3']bicarbazolyl (Compound 26)

9-Phenyl-9H,9'H-[3,3']bicarbazolyl (12.9 g), 4-bromo-iodobenzene (13.4 g), a copper powder (0.64 g), potassium carbonate (8.34 g), sodium bisulfite (0.49 g), and orthodichlorobenzene (50 ml) were added to a nitrogen-substituted reaction vessel, heated, and stirred at 170° C. for 19.5 hours. The mixture was cooled to 90° C., and dissolved after adding toluene (200 ml). After removing the insolubles by filtration, the filtrate was concentrated under reduced pressure, and crystallized from methanol (50 ml) to obtain a white powder of 9-(4-bromophenyl)-9'-phenyl-9H,9'H-[3,3']bicarbazolyl (17.30 g; yield 97%).

The resulting 9-(4-bromophenyl)-9'-phenyl-9H,9'H-[3,3'] bicarbazolyl (17.00 g), 9-phenyl-3-(4,4,5,5-tetramethyl-1,3,2-dioxabororan-2-yl)-9H-carbazole (12.25 g), toluene (160 ml), ethanol (40 ml), and a 2 M potassium carbonate aqueous solution (23 ml) were added to a nitrogen-substituted reaction vessel, and aerated with nitrogen gas for 30 minutes under ultrasonic waves. After adding tetrakis(triphenylphosphine) palladium (1.74 g), the mixture was heated, and stirred at 72° C. for 12.5 hours. The mixture was allowed to cool to room temperature, and extraction was performed by adding toluene (100 ml) and water (150 ml) thereto. The organic layer was dried over magnesium sulfate, and concentrated under reduced pressure to obtain a black crude product. The crude product was purified by column chromatography (carrier: silica gel; eluent: hexane/toluene) to obtain a pale yellowish white powder of 9'-phenyl-9-[4-(9-phenyl-9H-carbazol-3-yl)-phenyl]-9H,9'H-[3,3']bicarbazolyl (10.44 g; yield 48%).

Figure 2:
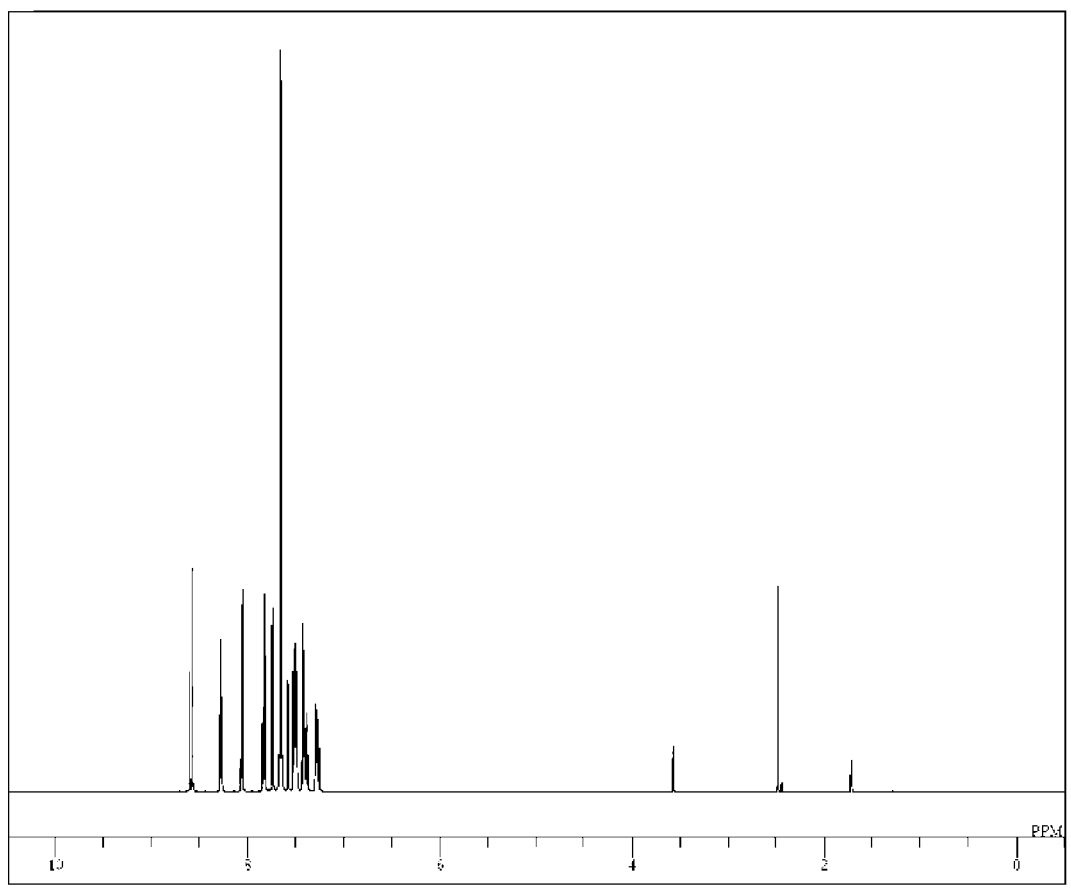
FIG. 2 is a ¹H-NMR chart of the compound of Example 2 of the present invention (Compound 26).

The structure of the resulting pale yellowish white powder was identified by NMR. The $^1$H-NMR measurement result is presented in FIG. 2.

1H-NMR (THF-d$_8$) detected 35 hydrogen signals, as follows. δ(ppm)=7.25-7.31 (3H), 7.36-7.44 (5H), 7.48-7.53 (5H), 7.58 (1H), 7.64-7.69 (8H), 7.73-7.76 (2H), 7.81-7.85 (3H), 8.04-8.08 (2H), 8.26-8.30 (3H), 8.56-8.61 (3H).

Example 3

The glass transition points of the compounds used in the present invention were determined using a high-sensitive differential scanning calorimeter DSC 3100S produced by Bruker AXS.

|  | Glass transition point |
|---|---|
| Compound of Example 1 of the present invention | 142.5° C. |
| Compound of Example 2 of the present invention | 151.4° C. |

The compounds used in the present invention have glass transition points of 100° C. or higher, demonstrating that the compounds used in the present invention have a stable thin-film state.

Example 4

A 100 nm-thick vapor-deposited film was fabricated on an ITO substrate using the compounds used in the present invention, and the work function was measured using an atmosphere photoelectron spectrometer (Model AC-3 produced by Riken Keiki Co., Ltd.).

|  | Work function |
|---|---|
| Compound of Example 1 of the present invention | 5.44 eV |
| Compound of Example 2 of the present invention | 5.49 eV |

As the results show, the compounds used in the present invention have desirable energy levels compared to the work function 5.4 eV of common hole transport materials such as α-NPD and TPD, and thus possess desirable hole transportability.

Example 5

A $1.0\times10^{-5}$ mol/L 2-methyltetrahydrofuran solution was prepared for the compounds used in the present invention. The prepared solution was placed in a designated quartz tube, and aerated with pure nitrogen to remove the oxygen content. The tube was plugged with a septum rubber to prevent mixing with oxygen. After being cooled to 77 K, the solution was irradiated with excitation light to measure the phosphorescence spectrum, using a spectrofluorometer FluoroMax-4 produced by Horiba Ltd. The wavelength of the first peak on the shorter wavelength side of the phosphorescence spectrum was taken, and the wavelength value was converted to light energy to calculate $T_1$.

|  | $T_1$ |
|---|---|
| Compound of Example 1 of the present invention | 2.74 eV |
| Compound of Example 2 of the present invention | 2.71 eV |
| FIrpic | 2.62 eV |
| Ir (ppy)$_3$ | 2.42 eV |
| CBP | 2.56 eV |
| α-NPD | 2.29 eV |

As can be seen, the compounds used in the present invention have higher $T_1$ values than commonly used blue phosphorescent material FIrpic, green phosphorescent material Ir(ppy)$_3$, commonly used host material CBP, and commonly used hole transport material α-NPD, and thus have sufficient capability for the confinement of the triplet excitons excited in the light emitting layer.

Example 6

Figure 3:
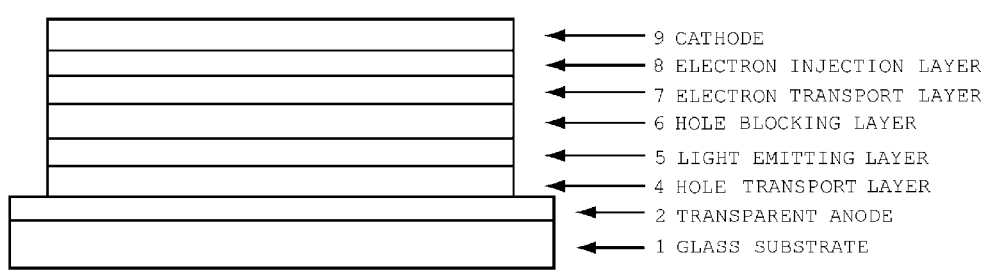
FIG. 3 is a diagram representing the configuration of the organic EL devices of Examples 6 and 7 and Comparative Examples 1 and 2.

The organic EL device, as illustrated in FIG. 3, was fabricated from a hole transport layer 4, a light emitting layer 5, a hole blocking layer 6, an electron transport layer 7, an electron injection layer 8, and a cathode (aluminum electrode) 9 successively formed by vapor deposition on a glass substrate 1 that had been provided beforehand with an ITO electrode as a transparent anode 2.

Specifically, the glass substrate 1 having ITO (thickness 150 nm) formed thereon was washed with an organic solvent, and subjected to an oxygen plasma treatment to wash the surface. The glass substrate with the ITO electrode was then installed in a vacuum vapor deposition apparatus, and the pressure was reduced to 0.001 Pa or less. This was followed by formation of the hole transport layer 4 by forming the compound of Example 1 of the present invention (Compound 5) over the transparent anode 2 in a thickness of 50 nm. Thereafter, the light emitting layer 5 was formed on the hole transport layer 4 by forming TPBI and Ir(ppy)$_3$ in a thickness of 20 nm using dual vapor deposition at a deposition rate ratio of TPBI:Ir(ppy)$_3$=92:8. The hole blocking layer 6 was then formed on the light emitting layer 5 by forming BCP in a thickness of 10 nm. Then, the electron transport layer 7 was formed on the hole blocking layer 6 by forming Alq$_3$ in a thickness of 30 nm. The electron injection layer 8 was then formed on the electron transport layer 7 by forming lithium fluoride in a thickness of 0.5 nm. Finally, the cathode 9 was formed by vapor depositing aluminum in a thickness of 150 nm. The characteristics of the organic EL device thus fabricated were measured in an atmosphere at ordinary temperature. Table 1 summarizes the results of the emission characteristics measurements performed by applying a DC voltage to the organic EL device.

Example 7

An organic EL device was fabricated under the same conditions used in Example 6, except that the compound of Example 2 of the present invention (Compound 26) was used as the material of the hole transport layer 4 of Example 6. The characteristics of the organic EL device thus fabricated were measured in an atmosphere at ordinary temperature. Table 1 summarizes the results of the emission characteristics measurements performed by applying a DC voltage to the organic EL device.

Comparative Example 1

For comparison, an organic EL device was fabricated under the same conditions used in Example 6, except that α-NPD was used as the material of the hole transport layer 4 of Example 6. The characteristics of the organic EL device thus fabricated were measured in an atmosphere at ordinary temperature. Table 1 summarizes the results of the emission characteristics measurements performed by applying a DC voltage to the organic EL device.

Comparative Example 2

For comparison, an organic EL device was fabricated under the same conditions used in Example 6, except that Compound 54 of the following structural formula was used as the material of the hole transport layer 4 of Example 6. The characteristics of the organic EL device thus fabricated were measured in an atmosphere at ordinary temperature. Table 1 summarizes the results of the emission characteristics measurements performed by applying a DC voltage to the organic EL device.

[Chemical Formula 67]

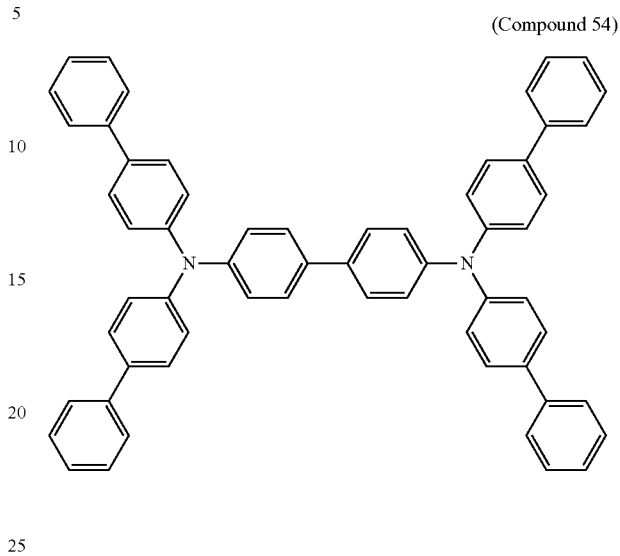

(Compound 54)

Example 8

Figure 4:
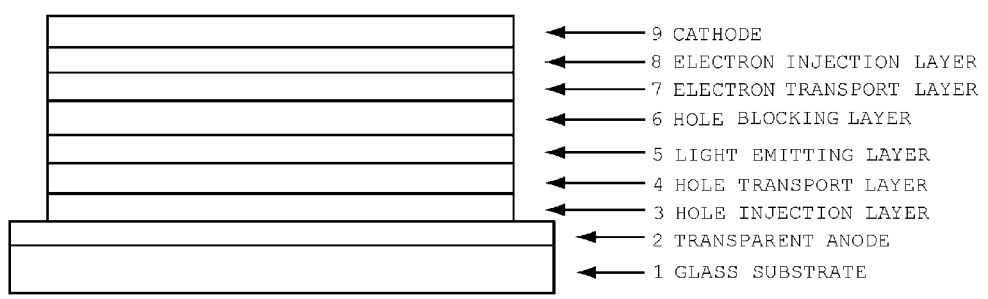
FIG. 4 is a diagram representing the configuration of the organic EL devices of Example 8 and Comparative Examples 3 and 4.

The organic EL device, as illustrated in FIG. 4, was fabricated from a hole injection layer 3, a hole transport layer 4, a light emitting layer 5, a hole blocking layer 6, an electron transport layer 7, an electron injection layer 8, and a cathode (aluminum electrode) 9 successively formed by vapor deposition on a glass substrate 1 that had been provided beforehand with an ITO electrode as a transparent anode 2.

Specifically, the glass substrate 1 having ITO (thickness 150 nm) formed thereon was washed with an organic solvent, and subjected to an oxygen plasma treatment to wash the surface. The glass substrate with the ITO electrode was then installed in a vacuum vapor deposition apparatus, and the pressure was reduced to 0.001 Pa or less. This was followed by formation of the hole injection layer 3 by forming Compound 55 of the structural formula below over the transparent anode 2 in a thickness of 20 nm. Thereafter, the hole transport layer 4 was formed on the hole injection layer 3 by forming the compound of Example 1 of the present invention (Compound 5) in a thickness of 30 nm. Then, the light emitting layer 5 was formed on the hole transport layer 4 in a thickness of 20 nm by forming TPBI and Ir(ppy)$_3$ using dual vapor deposition at a deposition rate ratio of TPBI:Ir(ppy)$_3$=92:8. The hole blocking layer 6 was then formed on the light emitting layer 5 by forming BCP in a thickness of 10 nm. Then, the electron transport layer 7 was formed on the hole blocking layer 6 by forming Alq$_3$ in a thickness of 30 nm. The electron injection layer 8 was then formed on the electron transport layer 7 by forming lithium fluoride in a thickness of 0.5 nm. Finally, the cathode 9 was formed by vapor depositing aluminum in a thickness of 150 nm. The characteristics of the organic EL device thus fabricated were measured in an atmosphere at ordinary temperature. Table 1 summarizes the results of the emission characteristics measurements performed by applying a DC voltage to the organic EL device.

[Chemical Formula 68]

(Compound 55)

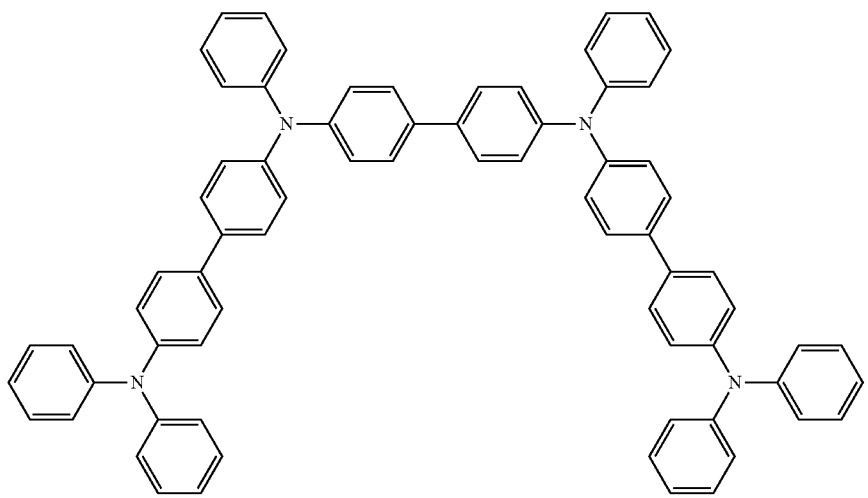

Comparative Example 3

For comparison, an organic EL device was fabricated under the same conditions used in Example 8, except that α-NPD was used as the material of the hole transport layer of Example 8. The characteristics of the organic EL device thus fabricated were measured in an atmosphere at ordinary temperature. Table 1 summarizes the results of the emission characteristics measurements performed by applying a DC voltage to the organic EL device.

Comparative Example 4

For comparison, an organic EL device was fabricated under the same conditions used in Example 8, except that the Compound 54 was used as the material of the hole transport layer 4 of Example 8. The characteristics of the organic EL device thus fabricated were measured in an atmosphere at ordinary temperature. Table 1 summarizes the results of the emission characteristics measurements performed by applying a DC voltage to the organic EL device.

As can be seen in Table 1, the driving voltage upon passing a current with a current density of 10 mA/cm$^2$ was 5.41 V for the compound of Example 1 of the present invention (Compound 5) and 5.52 V for the compound of the Example 2 of the present invention (Compound 26) used as the material of the hole transport layer, lower than 6.54 V or 5.89 V of when α-NPD or Compound 54 was used as the material of the hole transport layer. Further, the emission luminance, current efficiency, and power efficiency all greatly improved when the compound of Example 1 of the present invention (Compound 5) and the compound of Example 2 of the present invention (Compound 26) were used than when α-NPD and Compound 54 were used.

Further, the driving voltage lowered without affecting emission luminance, current efficiency, and power efficiency when Compound 55 was used as the material of the hole injection layer.

The results of turn on voltage measurements using the foregoing organic EL devices are presented below.

TABLE 1

|  | Hole injection layer material/hole transport layer material | Voltage [V] (@ 10 mA/cm$^2$) | Luminance [cd/m$^2$] (@ 10 mA/cm$^2$) | Current efficiency [cd/A] (@ 10 mA/cm$^2$) | Power efficiency [lm/W] (@ 10 mA/cm$^2$) |
|---|---|---|---|---|---|
| Ex. 6 | None/Compound 5 | 5.41 | 3039 | 30.41 | 17.65 |
| Ex. 7 | None/Compound 26 | 5.52 | 3419 | 34.25 | 19.51 |
| Com. Ex. 1 | None/α-NPD | 6.54 | 1931 | 19.33 | 9.25 |
| Com. Ex. 2 | None/Compound 54 | 5.89 | 1896 | 18.98 | 10.23 |
| Ex. 8 | Compound 55/ Compound 5 | 5.23 | 3118 | 31.20 | 18.73 |
| Com. Ex. 3 | Compound 55/ α-NPD | 6.46 | 1928 | 19.29 | 9.31 |
| Com. Ex. 4 | Compound 55/ Compound 54 | 5.74 | 1765 | 17.79 | 9.76 |

| Organic EL device | Hole injection layer material/ hole transport layer material | Turn on voltage [V] |
|---|---|---|
| Example 6 | None/Compound 5 | 2.7 |
| Example 7 | None/Compound 26 | 2.8 |
| Example 8 | Compound 55/Compound 5 | 2.7 |
| Comparative Example 1 | None/α-NPD | 2.9 |
| Comparative Example 2 | None/Compound 54 | 2.9 |
| Comparative Example 3 | Compound 55/α-NPD | 2.8 |
| Comparative Example 4 | Compound 55/Compound 54 | 2.8 |

It can be seen that the turn on voltage was lower in Examples 6 to 8 than in Comparative Examples 1 and 2 in which α-NPD and Compound 54, respectively, were used.

As these results demonstrate, the organic EL devices in which the compound of general formula (1) having a carbazole ring structure used in the present invention is used as the material of the hole transport layer can have improved emission luminance, luminous efficiency, and power efficiency, and a lower actual driving voltage, compared to the organic EL devices in which the known α-NPD and the Compound 54 were used as the material of the hole transport layer. It was also found that the driving voltage could be further lowered without affecting emission luminance, luminous efficiency, and power efficiency when an arylamine compound (the Compound 55) of a structure in which three or more triphenylamine structures are joined to each other within the molecule via a single bond or a divalent group that does not contain a heteroatom is used as the material of the hole injection layer.

INDUSTRIAL APPLICABILITY

The organic EL device produced by using the compound of general formula (1) having a carbazole ring structure can have high emission luminance, high luminous efficiency, and high power efficiency, and can have a low actual driving voltage to improve durability. There are potential applications for, for example, home electronic appliances and illuminations.

DESCRIPTION OF REFERENCE NUMERALS AND SIGNS

1 Glass substrate
2 Transparent anode
3 Hole injection layer
4 Hole transport layer
5 Light emitting layer
6 Hole blocking layer
7 Electron transport layer
8 Electron injection layer
9 Cathode

The invention claimed is:

1. An organic electroluminescent device comprising a pair of electrodes, and a plurality of organic layers sandwiched between the pair of electrodes and including a phosphorescent light-emitting material-containing light emitting layer and a hole transport layer,
  wherein a compound of the following general formula (1) having a carbazole ring structure is used as a constituent material of the hole transport layer,

[Chemical Formula 1]

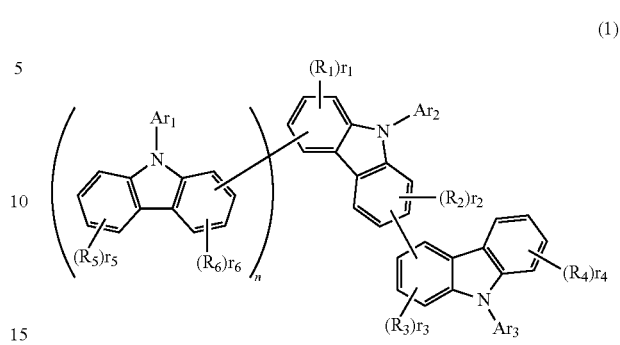

(1)

wherein R1, R2, R3, R4, R5, and R6 may be the same or different, and represent a fluorine atom, a chlorine atom, cyano, trifluoromethyl, nitro, linear or branched alkyl of 1 to 6 carbon atoms, cycloalkyl of 5 to 10 carbon atoms, linear or branched alkyloxy of 1 to 6 carbon atoms, cycloalkyloxy of 5 to 10 carbon atoms, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, r1, r4, and r5 represent 0 or an integer of 1 to 4, r2, r3, and r6 represent 0 or an integer of 1 to 3, n represents 1, Ar1, Ar2, and Ar3 may be the same or different, and represent a substituted or unsubstituted aromatic hydrocarbon group, a substituted or unsubstituted aromatic heterocyclic group, or a substituted or unsubstituted condensed polycyclic aromatic group,
and wherein, when Ar1 is a substituted aromatic hydrocarbon group, the substituent is a fluorine atom, a chlorine atom, cyano, trifluoromethyl, nitro, cycloalkyl of 5 to 10 carbon atoms, linear or branched alkenyl of 2 to 6 carbon atoms, linear or branched alkyloxy of 1 to 6 carbon atoms, cycloalkyloxy of 5 to 10 carbon atoms, phenyl, naphthyl, anthryl, styryl, phenoxy, tolyloxy, benzyloxy, or phenethyloxy, each of which may be further substituted.

2. The organic electroluminescent device of claim 1 in which the compound having a carbazole ring structure is used as a constituent material of the hole transport layer, wherein Ar2 in the general formula (1) is a monovalent group represented by the following general formula (2) or (3),

[Chemical Formula 2]

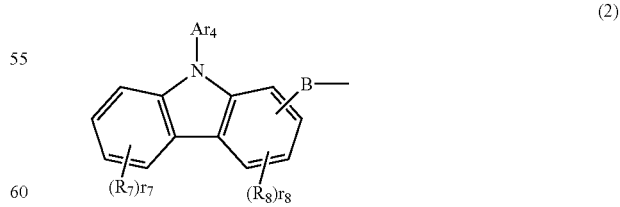

(2)

wherein R7 and R8 may be the same or different, and represent a fluorine atom, a chlorine atom, cyano, trifluoromethyl, nitro, linear or branched alkyl of 1 to 6 carbon atoms, cycloalkyl of 5 to 10 carbon atoms, linear or branched alkyloxy of 1 to 6 carbon atoms, cycloalkyloxy of 5 to 10 carbon atoms, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, r7 represents 0 or an integer of 1 to 4, r8 represents 0 or an integer of 1 to 3, B represents a divalent group of a substituted or unsubstituted aromatic hydrocarbon, a divalent group of a substituted or unsubstituted aromatic heterocyclic ring, or a divalent group of a substituted or unsubstituted condensed polycyclic aromatic, Ar4 represents a substituted or unsubstituted aromatic hydrocarbon group, a substituted or unsubstituted aromatic heterocyclic group, or a substituted or unsubstituted condensed polycyclic aromatic group,

[Chemical Formula 3]

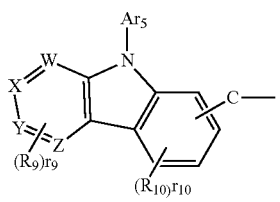

(3)

wherein R9 and R10 may be the same or different, and represent a fluorine atom, a chlorine atom, cyano, trifluoromethyl, nitro, linear or branched alkyl of 1 to 6 carbon atoms, cycloalkyl of 5 to 10 carbon atoms, linear or branched alkyloxy of 1 to 6 carbon atoms, cycloalkyloxy of 5 to 10 carbon atoms, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, r9 and r10 represent 0 or an integer of 1 to 3, C represents a divalent group of a substituted or unsubstituted aromatic hydrocarbon, a divalent group of a substituted or unsubstituted aromatic heterocyclic ring, or a divalent group of a substituted or unsubstituted condensed polycyclic aromatic, Ar5 represents a substituted or unsubstituted aromatic hydrocarbon group, a substituted or unsubstituted aromatic heterocyclic group, or a substituted or unsubstituted condensed polycyclic aromatic group, W, X, Y, and Z represent a carbon atom or a nitrogen atom, where only one of W, X, Y, and Z is a nitrogen atom, and, in this case, the nitrogen atom does not have the substituent R9.

3. The organic electroluminescent device of claim 1 comprising a pair of electrodes, and a plurality of organic layers sandwiched between the pair of electrodes and including a phosphorescent light-emitting material-containing light emitting layer and a hole transport layer, wherein a compound of the following general formula (1″) having a carbazole ring structure is used as a constituent material of the hole transport layer,

[Chemical Formula 5]

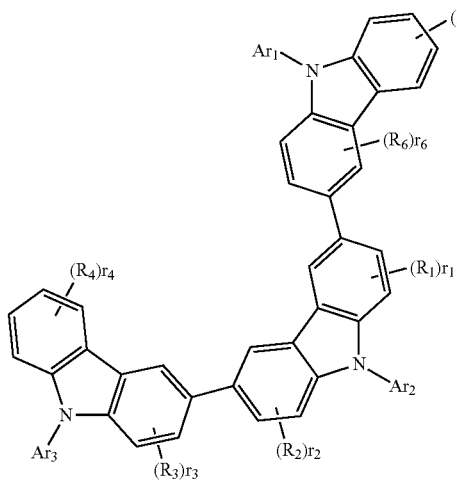

(1″)

wherein R1, R2, R3, R4, R5, and R6 may be the same or different, and represent a fluorine atom, a chlorine atom, cyano, trifluoromethyl, nitro, linear or branched alkyl of 1 to 6 carbon atoms, cycloalkyl of 5 to 10 carbon atoms, linear or branched alkyloxy of 1 to 6 carbon atoms, cycloalkyloxy of 5 to 10 carbon atoms, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, r4 and r5 represent 0 or an integer of 1 to 4, r1, r2, r3, and r6 represent 0 or an integer of 1 to 3, Ar1, Ar2, and Ar3 may be the same or different, and represent a substituted or unsubstituted aromatic hydrocarbon group, a substituted or unsubstituted aromatic heterocyclic group, or a substituted or unsubstituted condensed polycyclic aromatic group and wherein, when Ar1 is a substituted aromatic hydrocarbon group, the substituent is a fluorine atom, a chlorine atom, cyano, trifluoromethyl, nitro, cycloalkyl of 5 to 10 carbon atoms, linear or branched alkenyl of 2 to 6 carbon atoms, linear or branched alkyloxy of 1 to 6 carbon atoms, cycloalkyloxy of 5 to 10 carbon atoms, phenyl, naphthyl, anthryl, styryl, phenoxy, tolyloxy, benzyloxy, or phenethyloxy, each of which may be further substituted.

4. The organic electroluminescent device according to claim 1, wherein the organic layer is a hole injection layer, and the hole injection layer contains an arylamine compound of a structure in which three or more triphenylamine structures are joined to each other within the molecule via a divalent group that does not contain a heteroatom, or via a single bond.

5. The organic electroluminescent device according to claim 4, wherein the arylamine compound contained in the hole injection layer and having a structure in which three or more triphenylamine structures are joined to each other within the molecule via a divalent group that does not contain a heteroatom, or via a single bond is an arylamine compound represented by the following general formula (4),

[Chemical Formula 6]

(4)

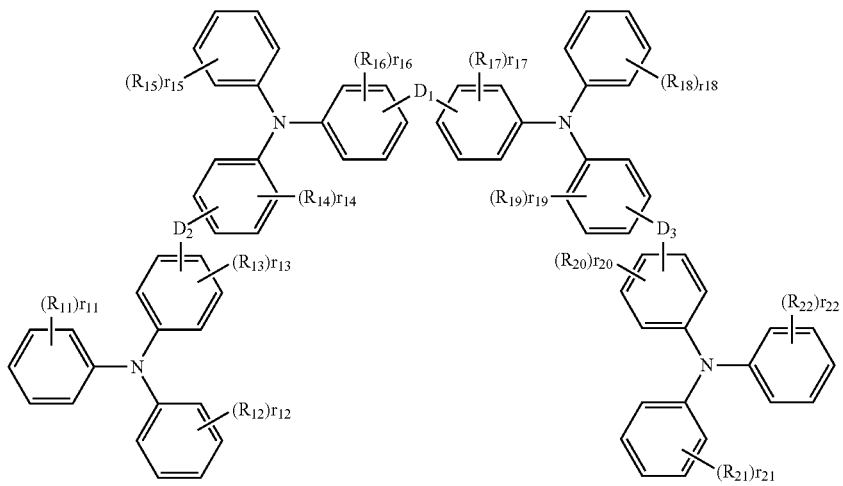

wherein R11 to R22 may be the same or different, and represent a fluorine atom, a chlorine atom, cyano, trifluoromethyl, linear or branched alkyl of 1 to 6 carbon atoms, linear or branched alkenyl of 2 to 6 carbon atoms, a substituted or unsubstituted aromatic hydrocarbon group, a substituted or unsubstituted aromatic heterocyclic group, or a substituted or unsubstituted condensed polycyclic aromatic group, where these substituents may together form a ring when a plurality of these substituents are joined to the same benzene ring, and wherein r11 to r22 represent 0 or an integer of 1 to 4, D1, D2, and D3 may be the same or different, and represent a divalent group of the following structural formulae (E) to (I), or a single bond,

[Chemical Formula 7]

(E)

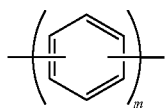

wherein m represents an integer of 1 to 3,

[Chemical Formula 8]

(F)

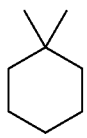

[Chemical Formula 9]

(G)

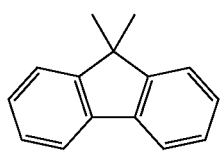

[Chemical Formula 10]

-continued (H)

—CH$_2$—

[Chemical Formula 11]

(I)

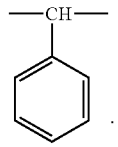

6. An organic electroluminescent device comprising a pair of electrodes, and a plurality of organic layers sandwiched between the pair of electrodes and including a phosphorescent light-emitting material-containing light emitting layer, a hole injection layer, and a hole transport layer,
wherein a compound of the general formula (1) having a carbazole ring structure is used as a constituent material of the hole injection layer (1)

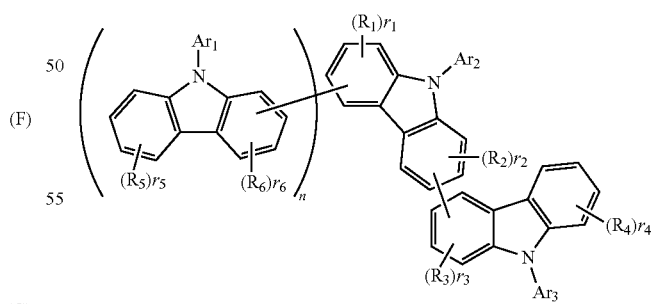

wherein R1, R2, R3, R4, R5, and R6 may be the same or different, and represent a fluorine atom, a chlorine atom, cyano, trifluoromethyl, nitro, linear or branched alkyl of 1 to 6 carbon atoms, cycloalkyl of 5 to 10 carbon atoms, linear or branched alkyloxy of 1 to 6 carbon atoms, cycloalkyloxy of 5 to 10 carbon atoms, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, r1, r4, and r5 represent 0 or an integer of 1 to 4, r2, r3, and r6 represent 0 or an integer of 1 to 3, n represents 1, Ar1, Ar2, and Ar3 may be the same or different, and represent a substituted or unsubstituted aromatic hydrocarbon group, a substituted or unsubstituted aromatic heterocyclic group, or a substituted or unsubstituted condensed polycyclic aromatic group, and wherein, when Ar1 is a substituted aromatic hydrocarbon group, the substituent is a fluorine atom, a chlorine atom, cyano, trifluoromethyl, nitro, cycloalkyl of 5 to 10 carbon atoms, linear or branched alkenyl of 2 to 6 carbon atoms, linear or branched alkyloxy of 1 to 6 carbon atoms, cycloalkyloxy of 5 to 10 carbon atoms, phenyl, naphthyl, anthryl, styryl, phenoxy, tolyloxy, benzyloxy, or phenethyloxy, each of which may be further substituted.

7. The organic electroluminescent device according to claim 1, wherein the phosphorescent light-emitting material is a metal complex that contains iridium or platinum.

8. The organic electroluminescent device according to claim 2, wherein the organic layer is a hole injection layer, and the hole injection layer contains an arylamine compound of a structure in which three or more triphenylamine structures are joined to each other within the molecule via a divalent group that does not contain a heteroatom, or via a single bond.

9. The organic electroluminescent device according to claim 3, wherein the organic layer is a hole injection layer, and the hole injection layer contains an arylamine compound of a structure in which three or more triphenylamine structures are joined to each other within the molecule via a divalent group that does not contain a heteroatom, or via a single bond.

10. The organic electroluminescent device according to claim 8, wherein the arylamine compound contained in the hole injection layer and having a structure in which three or more triphenylamine structures are joined to each other within the molecule via a divalent group that does not contain a heteroatom, or via a single bond is an arylamine compound represented by the following general formula (4),

[Chemical Formula 6]

wherein R11 to R22 may be the same or different, and represent a fluorine atom, a chlorine atom, cyano, trifluoromethyl, linear or branched alkyl of 1 to 6 carbon atoms, linear or branched alkenyl of 2 to 6 carbon atoms, a substituted or unsubstituted aromatic hydrocarbon group, a substituted or unsubstituted aromatic heterocyclic group, or a substituted or unsubstituted condensed polycyclic aromatic group, where these substituents may together form a ring when a plurality of these substituents are joined to the same benzene ring, and wherein r11 to r22 represent 0 or an integer of 1 to 4, D1, D2, and D3 may be the same or different, and represent a divalent group of the following structural formulae (E) to (I), or a single bond,

[Chemical Formula 7]

(E)

wherein m represents an integer of 1 to 3,

[Chemical Formula 8]

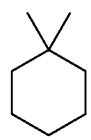

(F)

[Chemical Formula 9]

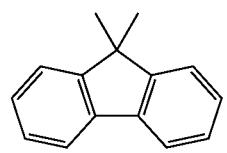

(G)

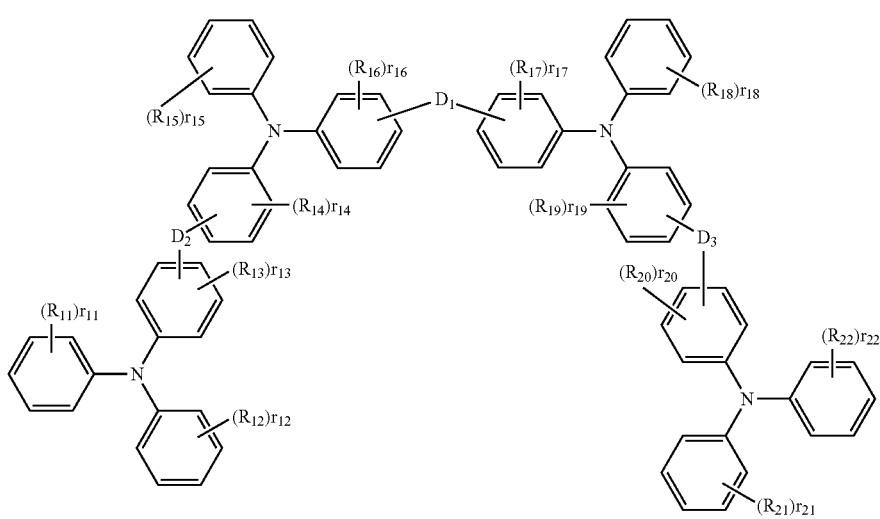

(4)

[Chemical Formula 10]

(H)

[Chemical Formula 11]

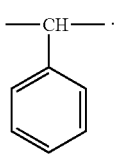
(I)

11. The organic electroluminescent device according to claim 9, wherein the arylamine compound contained in the hole injection layer and having a structure in which three or more triphenylamine structures are joined to each other within the molecule via a divalent group that does not contain a heteroatom, or via a single bond is an arylamine compound represented by the following general formula (4),

[Chemical Formula 6]

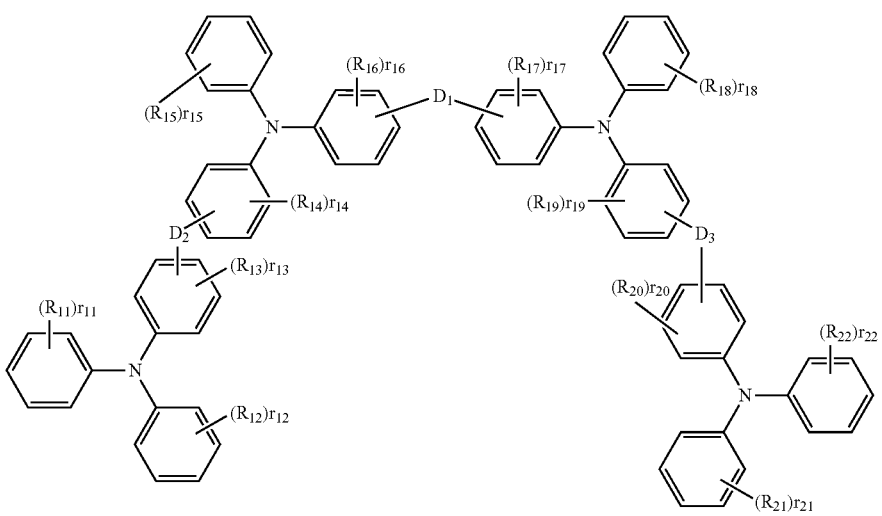
(4)

wherein R11 to R22 may be the same or different, and represent a fluorine atom, a chlorine atom, cyano, trifluoromethyl, linear or branched alkyl of 1 to 6 carbon atoms, linear or branched alkenyl of 2 to 6 carbon atoms, a substituted or unsubstituted aromatic hydrocarbon group, a substituted or unsubstituted aromatic heterocyclic group, or a substituted or unsubstituted condensed polycyclic aromatic group, where these substituents may together form a ring when a plurality of these substituents are joined to the same benzene ring, and wherein r11 to r22 represent 0 or an integer of 1 to 4, D1, D2, and D3 may be the same or different, and represent a divalent group of the following structural formulae (E) to (I), or a single bond,

[Chemical Formula 7]

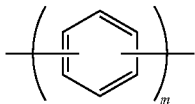
(E)

wherein m represents an integer of 1 to 3,

[Chemical Formula 8]

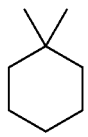
(F)

[Chemical Formula 9]

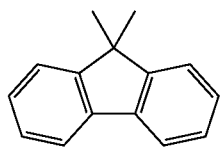
(G)

-continued

[Chemical Formula 10]

(H)

—CH$_2$—

[Chemical Formula 11]

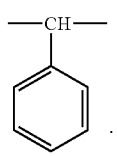
(I)

12. The organic electroluminescent device according to claim 2, wherein the phosphorescent light-emitting material is a metal complex that contains iridium or platinum.

13. The organic electroluminescent device according to claim 3, wherein the phosphorescent light-emitting material is a metal complex that contains iridium or platinum.

* * * * *